US010773075B2

(12) United States Patent
Pepin et al.

(10) Patent No.: US 10,773,075 B2
(45) Date of Patent: Sep. 15, 2020

(54) NEURAL ELECTRODE ARRAY ATTACHMENT

(71) Applicant: Verily Life Sciences LLC, South San Francisco, CA (US)

(72) Inventors: Brian Pepin, San Francisco, CA (US); Peng Cong, Burlingame, CA (US); Kedar Shah, San Francisco, CA (US); Shivkumar Sabesan, San Mateo, CA (US)

(73) Assignee: VERILY LIFE SCIENCES LLC, South San Francisco, CA (US)

( * ) Notice: Subject to any disclaimer, the term of this patent is extended or adjusted under 35 U.S.C. 154(b) by 123 days.

(21) Appl. No.: 15/925,953

(22) Filed: Mar. 20, 2018

(65) Prior Publication Data

US 2018/0272126 A1    Sep. 27, 2018

Related U.S. Application Data

(60) Provisional application No. 62/474,703, filed on Mar. 22, 2017, provisional application No. 62/555,387, filed on Sep. 7, 2017.

(51) Int. Cl.
*A61N 1/05* (2006.01)
*A61N 1/08* (2006.01)
*A61N 1/36* (2006.01)

(52) U.S. Cl.
CPC ............. *A61N 1/0558* (2013.01); *A61N 1/05* (2013.01); *A61N 1/0556* (2013.01); *A61N 1/08* (2013.01); *A61N 1/36* (2013.01)

(58) Field of Classification Search
CPC ...... A61N 1/05–0597; A61N 1/08–086; A61N 1/36–3787; A41D 2400/324; A61H 39/08; A61H 39/086
See application file for complete search history.

(56) References Cited

U.S. PATENT DOCUMENTS 4,969,468 A    11/1990  Byers et al.
5,215,088 A *   6/1993  Normann ........... A61B 5/04001
                                                600/377
(Continued)

OTHER PUBLICATIONS

Verdecchia, Nicole, Vladyslav Melnyk, Joseph Pichamuthu, David Vorp, and Steven Orebaugh. "The Physical Relationship of the Sciatic Nerve and Its Paraneural Sheath." the Anesthesiology annual meeting. American Society of Anesthesiologists, Oct. 23, 2016. http://www.asaabstracts.com/strands/asaabstracts/abstract.*

(Continued)

*Primary Examiner* — Tan-Uyen T Ho
*Assistant Examiner* — Charles M Wei
(74) *Attorney, Agent, or Firm* — Kilpatrick Townsend & Stockton LLP

(57) ABSTRACT

An electrode cuff for placement around a peripheral nerve can include one or more protrusions extending from a tissue-contacting surface of the electrode cuff. A protrusion can include one or more electrodes and can have a blunt distal end. The protrusion(s) can be driven into the nerve using a driving tool designed to apply mechanical oscillations and/or swift mechanical force to the electrode cuff. The mechanical oscillations and/or swift mechanical force can insert the blunt distal ends of the protrusions into the nerve without damaging fascicles within the nerve. During implantation, a sensor associated with the driving tool and/or the electrode cuff can provide dynamic feedback to a controller for controlling the driving tool. The sensor may detect pressure, temperature, acoustic activity, and/or electrical activity to indicate when the protrusions have pierced the epineurium, allowing the controller to cease the driving tool and thus avoid damage to the fascicles.

17 Claims, 15 Drawing Sheets

(56) References Cited

U.S. PATENT DOCUMENTS

| | | | | |
|---|---|---|---|---|
| 5,400,784 | A * | 3/1995 | Durand | A61N 1/0556 29/825 |
| 5,634,462 | A * | 6/1997 | Tyler | A61N 1/0556 600/377 |
| 5,824,027 | A * | 10/1998 | Hoffer | A61N 1/0556 607/118 |
| 5,919,220 | A * | 7/1999 | Stieglitz | A61N 1/0556 600/377 |
| 8,116,886 | B2 * | 2/2012 | Simaan | A61N 1/0541 607/137 |
| 8,452,418 | B2 | 5/2013 | Tang et al. | |
| 8,788,045 | B2 * | 7/2014 | Gross | A61N 1/36071 607/46 |
| 2004/0024439 | A1 | 2/2004 | Riso | |
| 2006/0155344 | A1 * | 7/2006 | Rezai | A61N 1/0551 607/46 |
| 2006/0206155 | A1 * | 9/2006 | Ben-David | A61N 1/0556 607/9 |
| 2007/0270712 | A1 * | 11/2007 | Wiksell | A61B 10/025 600/567 |
| 2008/0091183 | A1 * | 4/2008 | Knopp | A61B 18/1402 606/31 |
| 2009/0069712 | A1 * | 3/2009 | Mulvihill | A61B 10/025 600/564 |
| 2010/0023021 | A1 * | 1/2010 | Flaherty | A61B 5/0084 606/130 |
| 2010/0152811 | A1 * | 6/2010 | Flaherty | A61H 39/002 607/50 |
| 2010/0161019 | A1 * | 6/2010 | Clark | A61N 1/0556 607/116 |
| 2012/0078161 | A1 * | 3/2012 | Masterson | A61N 1/327 604/21 |
| 2013/0253299 | A1 * | 9/2013 | Weber | A61B 5/4519 600/377 |
| 2014/0323837 | A1 * | 10/2014 | Hirshberg | A61M 37/0015 600/365 |
| 2015/0141786 | A1 * | 5/2015 | Durand | A61B 5/04001 600/377 |
| 2016/0158533 | A1 * | 6/2016 | Jolly | A61N 1/05 600/377 |
| 2016/0235329 | A1 * | 8/2016 | Bernstein | A61B 8/48 |
| 2016/0361064 | A1 * | 12/2016 | Shah | A61B 17/1128 |
| 2017/0020403 | A1 * | 1/2017 | Kim | A61B 5/04001 |
| 2017/0105784 | A1 * | 4/2017 | Su | A61B 18/1233 |
| 2017/0172437 | A1 * | 6/2017 | Butera | A61B 5/6877 |
| 2017/0203100 | A1 * | 7/2017 | Imran | A61N 1/36007 |
| 2017/0367733 | A1 * | 12/2017 | Murphy | A61B 5/04 |
| 2018/0104478 | A1 * | 4/2018 | Hwang | A61B 18/14 |

OTHER PUBLICATIONS

International Application No. PCT/US2018/023416, "International Preliminary Report on Patentability," dated Oct. 3, 2019, 9 pages.
International Application No. PCT/US2018/023416 , "International Search Report and Written Opinion", dated Jun. 21, 2018, 13 pages, European Patent Office.

* cited by examiner

NEURAL ELECTRODE ARRAY ATTACHMENT

CROSS-REFERENCE TO RELATED APPLICATIONS

This application claims the benefit of and the priority to U.S. Provisional Application No. 62/474,703, filed on Mar. 22, 2017, and U.S. Provisional Application No. 62/555,387, filed on Sep. 7, 2017. Each of these applications is hereby incorporated by reference in its entirety for all purposes.

TECHNICAL FIELD

The present disclosure generally relates to medical devices and more specifically to electrode arrays, such as electrode arrays for neural stimulation.

BACKGROUND

Neural stimulation, such as peripheral nervous system (PNS) stimulation (e.g.,) techniques like vagal nerve stimulation (VNS), can provide therapy for many chronic diseases including epilepsy and depression. When stimulating nerves, such as in the PNS, it can be especially difficult to position electrodes to be in close proximity to nerve fascicles, at least because of the nerve's epineurium layer. As a result, electrical stimulation can be very inefficient.

Current design limitations with respect to electrode placement within a peripheral nerve also limit the ability to sense data associated with the nerve. Current PNS electrode placement options are inadequate for providing a sufficiently high signal-to-noise ratio of sensed neural activity. Current PNS electrode placement results in sensed signals frequently being largely overrun by other nearby electrical activity, such as electrocardial activity and electromuscular activity. As a result, current neural stimulation schemes generally operate in an open-loop fashion, without direct electrical feedback from the nerve.

Additionally, current techniques for PNS electrode placement often rely upon compressing the nerve between flat, opposing plates lined with sharp electrodes. Compression of the nerve into a flattened shape may allow the individual fascicles within the nerve to spread apart in the flat plane, thus allowing the plurality of electrodes to puncture the nerve at locations adjacent individual neurons. However, this technique is rudimentary at best and long-term use may result in complications due to compression of the nerve.

Some techniques for PNS electrode placement rely upon manual application of force to pierce the epineurium of the nerve, and possibly the perineurium of a fascicle. Manual application of force is generally performed relatively slowly, especially because of the risk of damaging surrounding tissue. Also, the force applied to pierce the epineurium can inadvertently damage the nerve, including the fascicles within. Some techniques attempt to minimize the amount of pressure applied during implantation, often relying on sharp electrodes to focus force onto a single point on the epineurium. While these sharp electrodes pierce the epineurium, they also carry a high risk of piercing or damaging a fascicle.

SUMMARY

The term embodiment and like terms are intended to refer broadly to all of the subject matter of this disclosure and the claims below. Statements containing these terms should be understood not to limit the subject matter described herein or to limit the meaning or scope of the claims below. Embodiments of the present disclosure covered herein are defined by the claims below, not this summary. This summary is a high-level overview of various aspects of the disclosure and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this disclosure, any or all drawings and each claim.

Embodiments of the present disclosure include an electrode placement system, comprising: a substrate having a tissue-facing surface curved in a concave shape; at least one electrode protrusion extending from the tissue-facing surface and including one or more individual electrodes thereon, each of the at least one electrode protrusion including a blunt distal end; and a driving tool positioned and configured to apply mechanical force to the substrate, the driving tool comprising an oscillating driver, a pneumatic driver, or both.

In some cases, the driving tool includes the oscillating driver for delivering oscillating mechanical force to the substrate of the electrode cuff. In some cases, the oscillating driver is an ultrasonic transducer. In some cases, the driving tool includes the pneumatic driver for applying swift mechanical force to the substrate of the electrode cuff. In some cases the pneumatic driver is configured to receive a source of compressed air to provide the mechanical force.

In some cases, the swift mechanical force is a force greater than 0.5 N. In some cases, the swift mechanical force is applied for less than 1 s. In some cases, the swift mechanical force exerts a force on the substrate of the electrode cuff that drives the electrode protrusions to penetrate a depth ranging from 2 µm to 20 µm of the nerve. In some cases, the swift mechanical force is a force greater than 0.5 N that is applied for less than 1 s. In some cases, the driving tool is integrated into the electrode cuff. In some cases, the driving tool is separable from or separate from the electrode cuff.

In some cases, the electrode placement system further comprises: a sensor coupled to the at least one electrode protrusion to measure an insertion-indicative value, the insertion-indicative value being indicative of whether the at least one electrode protrusion has penetrated at least part of the nerve; and a controller coupled to the sensor and the driving tool to control the driving tool in response to the measured value. In some cases, the sensor comprises an electrical sensor, a mechanical sensor, a temperature sensor, or an acoustic sensor. In some cases, the driving tool includes at least one pneumatic actuator, and the sensor is a pressure sensor for detecting pneumatic pressure applied to the at least one pneumatic actuator.

Embodiments of the present disclosure include a method of applying an electrode cuff to a target tissue, comprising: providing an electrode cuff comprising a substrate having a tissue-facing surface curved in a concave shape; at least one electrode protrusion extending from the tissue-facing surface and including one or more individual electrodes thereon, the at least one electrode protrusion includes a blunt distal end; and positioning the tissue-facing surface of the substrate against a nerve; and actuating a driving tool to apply a mechanical force to the electrode cuff to pierce the at least one protrusion into a nerve, wherein the driving tool is an oscillating driver, a pneumatic driver, or both.

In some cases, the method further comprises; measuring an insertion-indicative value, the insertion-indicative value being indicative of whether the at least one electrode protrusion has penetrated at least part of the nerve; wherein actuating the driving tool further comprises dynamically controlling the mechanical force applied to the substrate in response to the measured insertion-indicative value.

In some cases, the driving tool includes the oscillating driver. In some cases, actuating the oscillating driver comprises applying oscillating mechanical force to the electrode cuff to pierce the at least one protrusion into the nerve. In some cases, the driving tool includes the pneumatic driver. In some cases, actuating the pneumatic driver comprises applying swift mechanical force to the electrode cuff to pierce the at least one protrusion into the nerve. In some cases, the swift mechanical force is a force greater than 0.5 N that is applied for less than 1 s. In some cases, the driving tool is integrated into the electrode cuff.

BRIEF DESCRIPTION OF THE DRAWINGS

The specification makes reference to the following appended figures, in which use of like reference numerals in different figures is intended to illustrate like or analogous components.

DETAILED DESCRIPTION

Figure 1:
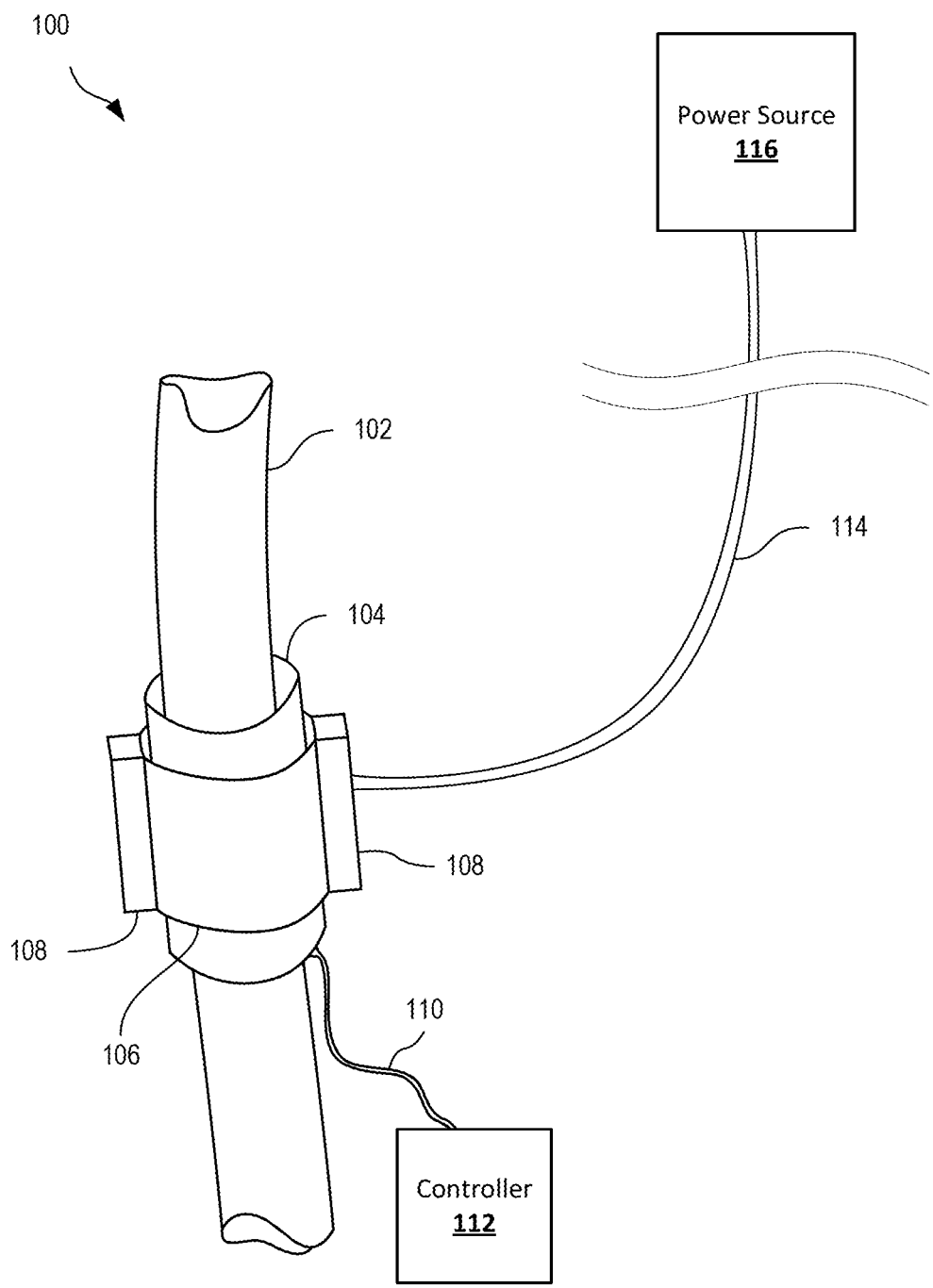
FIG. 1 is a schematic diagram of an electrode placement system securing an electrode cuff to a nerve according to certain aspects of the present disclosure.

Certain aspects and features of the present disclosure relate to an electrode cuff for placement on a nerve, such as for peripheral nerve stimulation or monitoring. The nerve cuff can have a curved shape matching the curvature of the nerve. Protrusions extending from a tissue-contacting surface of the electrode cuff can have one or more electrodes thereon, each of which can include a blunt distal end. The electrode cuff can be attached and the protrusions can be driven into the nerve using an oscillating driver and/or a pneumatic driver. An oscillating driver can provide mechanical oscillations to drive the protrusions into the nerve. A pneumatic driver can provide swift mechanical force to the substrate to drive electrode the protrusions into the nerve. The electrode cuff, once fully implanted, can result in its protrusions piercing the epineurium of the nerve without damaging nerve fascicles within.

In some cases, during installation, a sensor associated with the driving tool and/or the electrode cuff can provide feedback to a controller for controlling the driving tool. The sensor may coupled to the at least one electrode protrusion can measure an insertion-indicative value, e.g., pressure, temperature, acoustic activity, and/or electrical activity to indicate when the protrusions have pierced the epineurium, allowing the controller to cease the driving tool and thus avoid damage to the nerve fascicles. The insertion-indicative value may be indicative of whether the at least one electrode protrusion has penetrated at least part of the nerve. The controller may also be coupled to the sensor and the driving tool to control the driving tool in response to the measured insertion-indicative value.

In some cases, a sensor is coupled to the at least one electrode protrusion to measure a value indicative of insertion (e.g., an insertion-indicative value) of the at least one electrode protrusion into the nerve and a controller is coupled to the sensor and the driving tool to control the driving tool in response to the measured insertion-indicative value. In some cases, the sensor is an electrical sensor and the measured insertion-indicative value represents an electrical signal passing through at least one of the one or more individual electrodes. In some cases, the measured insertion-indicative value represents an electrical signal passing through the one or more individual electrodes of at least two of the at least one electrode protrusion. In some cases, the measured insertion-indicative value represents an electrical signal passing through at least two of the one or more individual electrodes of one of the at least one electrode protrusion. In some cases, the sensor is a mechanical sensor and the measured insertion-indicative value represents force applied by the driving tool. In some cases, the driving tool includes at least one pneumatic actuator, and wherein the sensor is a pressure sensor for detecting pneumatic pressure applied to the at least one pneumatic actuator. In some cases, the sensor is coupled to the at least one electrode protrusion indirectly.

The electrode cuff can be any suitable shape, including cylindrical or partially cylindrical. The electrode cuff can include a substrate having a tissue-contacting surface. In some cases, the tissue-contacting surface is an inner surface (e.g., closest to the nerve) opposite an outer surface of the substrate when the electrode cuff is wrapped around a nerve. The substrate can be single-layered or multi-layered. The substrate can be made of any suitable material.

In some cases, the tissue-contacting surface is shaped or contoured to match or correspond to a spatial characteristic (e.g., shape, diameter, size along one or more dimensions) of the nerve (e.g., the outer surface of the nerve). The tissue-contacting surface can be generally convex in shape. In some cases, the tissue-contacting surface is contoured, in part, due to changes in thicknesses of the substrate, and thus the outer surface of the substrate may have a different curvature than the tissue-contacting surface. In some cases, the entire substrate is shaped or contoured to match a shape of the nerve (e.g., the outer surface of the nerve). It will be appreciated that such matching may be performed based on general or average known nerve anatomy and need not be performed for specific nerves in specific individuals to be involved in a procedure. In some cases, the electrode cuff can have shape memory and/or a natural bias towards a primary position, in which the tissue-contacting surface has a convex shape (e.g., a contour matching the outer surface of the nerve). The electrode cuff can be manipulated out of the primary position to place the electrode cuff about the nerve by applying a manipulation pressure. Once placed about the nerve, release of manipulation pressure can allow the electrode cuff to naturally move to its primary position (e.g., wrapped snugly around the nerve).

In some embodiments, the substrate of the electrode cuff can be formed of a flexible, non-conductive material. Use of a flexible material can allow substrate to expand and contract as necessary to accommodate swelling of the nerve following implantation of electrode cuff system, and thereby prevent nerve damage and trauma. In exemplary embodiments, substrate can be made of silicone. In some embodiments, the substrate may be formed of a flexible polymer material (e.g., a thermoplastic), polyimide, liquid crystal polymer (LCP), or paraylene. In some embodiments, substrate is not a continuous sheet and can include discrete elements to accommodate swelling and/or growth of the target nerve and formation of scar tissue around the implantation site.

One or more electrode protrusions can extend from the tissue-contacting surface. The electrode protrusions can be made from the same material as the substrate or a different material. In some cases, the substrate and the electrode protrusions are monolithic. However in some cases the electrode protrusions can be otherwise coupled to the substrate. For example, electrode protrusions can be adhered to the substrate, can be embedded within the substrate, or can otherwise be attached to the substrate. Each electrode protrusion can include one or more electrodes. Electrodes can be embedded within the electrode protrusion or coupled to the surface of the electrode protrusion. In some cases, an electrode protrusion can be made of a conductive material and therefore act as an electrode itself. In some cases, an electrode protrusion made of a conductive material can be coated (or overcoated) with an insulating material over areas desired to remain non-conductive to surrounding tissue.

In some embodiments, the electrode protrusions and/or the electrodes can be made of a hard conductive material, e.g., conductive metals or alloys. In some embodiments, the electrode protrusions and/or the electrodes can be made of platinum, titanium, iridium, tungsten, gold, silver, copper or alloys thereof. In some embodiments, the bulk of the electrode protrusions can be made of one material and the electrode can be made of a different material. For example, in some embodiments, the electrodes can be made of conductive metals or alloys. In some exemplary embodiments, the bulks of the electrode protrusions can be insulated and electrodes can be exposed. For example, in some embodiments, the bulks of the electrode protrusions can be wrapped with a non-conductive polymer or silicone material leaving only the conductive electrodes exposed.

In some cases, the electrode protrusions can have sharp distal ends (e.g., the end of the electrode protrusion that first contacts the nerve during insertion) to puncture the epineurium membrane during insertion. However, it has been found that sharp distal ends can risk damaging fascicles within the nerve. It has been surprisingly determined that electrode protrusions with blunt distal ends can decrease the risk of damaging fascicles. However, it can be difficult to pierce the epineurium membrane with electrode protrusions having blunt distal ends.

Through trial and experimentation, it has been determined that electrode protrusions with blunt distal ends can nonetheless be used and can successfully and reliably pierce the epineurium membrane during implantation with the use of certain equipment and/or techniques as described herein, such as the use of oscillations or swift mechanical force to the substrate of the electrode cuff to drive the electrode protrusions into the nerve. In some cases, the electrode protrusions are sized to have a length suitable for penetrating the epineurium of the nerve, but not sufficiently long to damage fascicles therein. For example, the electrode protrusion can have a length smaller than a maximum limit after which damage to fascicles is likely to occur. In some cases, the electrode protrusions have a length in a range from 2 µm to 20 µm, e.g., from 4 µm to 16 µm, from 6 µm to 12 µm, or from 8 µm to 10 µm. In some cases, the electrode protrusions have a length less than 20 µm, e.g., less than 15 µm, less than 10 µm, or less than 5 µm. In terms of lower limits, the electrode protrusions have a length greater than 2 µm, e.g., greater than 5 µm, greater than 10 µm, or greater than 15 µm.

Implantation of the electrode cuff on a nerve can include positioning the electrode cuff around the nerve and then driving the electrode protrusions into the nerve, such as through an epineurium membrane of the nerve. Driving the electrode protrusions into the nerve can include (for example) using mechanical oscillations, swift mechanical force, or a combination thereof, to the substrate of the electrode cuff to drive the electrode protrusions.

Electrode protrusions can be driven into the nerve using mechanical oscillations. A mechanical oscillator, such as a mechanical transducer, can generate mechanical oscillations in the electrode protrusions. In some cases, the mechanical oscillator can be a part of a cuff device and/or included in the electrode cuff itself (e.g., coupled to or embedded within the substrate of the electrode cuff). In some cases, the mechanical oscillator can be included in a separable tool configured to engage the electrode cuff during implantation. Suitable tools can temporarily couple to the electrode cuff, can surround the electrode cuff, or can be placed against the electrode cuff during implantation. For example, a suitable tool can include a mechanical oscillator built into a clamping device designed to clamp the electrode cuff around the nerve. The use of mechanical oscillations can be combined with additional force applied to urge the electrode protrusions into the nerve.

As the electrode protrusions are being pushed against, and eventually driven into, the nerve, the mechanical oscillations within the electrode protrusions can generate mechanical oscillations in the epineurium of the nerve. These oscillations can pierce the blunt distal ends of the electrode protrusions into the nerve, without damage to fascicles inside. In some cases, mechanically oscillating electrode protrusions are simultaneously pushed towards the nerve from multiple sides.

In some cases, the mechanical oscillations can be ultrasonic (e.g., at or greater than 20 kHz), although any suitable frequency can be used. In some cases, the frequency and/or amplitude of the oscillations can be adjusted before or during implantation of the electrode cuff. For example, a frequency may increase during an electrode-insertion procedure until the electrode(s) have penetrated the epineurium and/or a maximum frequency has been reached.

In some instances, a driving tool is configured and/or operated in a manner that reduces contact with and/or damage to fascicles within the nerve. Specifically, a driving tool can be configured and/or operated such that electrode protrusions are driven so as to produce a swift mechanical force (e.g., to result in swift displacement) on a receiving structure (e.g., a nerve into which the electrode protrusions are driven). The swift mechanical force can be defined to be a force that is above a lower force threshold (e.g., 0.5 N) and that is applied for less than an upper time threshold (e.g., 1 second). The lower force threshold can facilitate successfully puncturing a first layer (e.g., the epineurium) of the receiving structure, while the upper time threshold can facilitate protecting one or more second structures (e.g., fascicles) of the receiving structure.

The use of swift mechanical force also facilitates effective use of electrode protrusions having blunt distal ends, which can further facilitate protecting nerve fascicles. Conventional electrode protrusions include the sharp distal ends, which can puncture a nerve's epineurium relatively easily. However, the sharp distal ends risk damaging fascicles within the nerve. It has been surprisingly determined that electrode protrusions with blunt distal ends can also successfully puncture a nerve's epineurium, when a swift mechanical force is exerted on the substrate of the electrode cuff. The swift mechanical force can include a force greater than that generally used with sharp electrodes and/or can correspond to a force-exertion time short than that generally used with sharp electrodes. Unlike situations where a normal force is repeatedly applied, applying swift mechanical force advantageously can quickly and efficiently pierce the epineurium in a single application. After penetrating the epineurium, the shape of the blunt distal ends and/or the shorter force-exertion time can have an effect of causing less damage to the fascicles as compared to use of traditional sharp electrodes.

Swift mechanical force can be a sufficient force applied for a short period of time that is sufficient to pierce the epineurium. In some cases, swift mechanical force is a force greater than 0.5 N applied for less than 1 s. It has been determined that the use of a pneumatic driver (e.g., pneumatic actuator) can be especially suitable for applying swift mechanical force to the substrate sufficient for the electrode protrusions to pierce through the epineurium membrane. Compressed fluid, such as compressed gas or compressed air, can be provided to the pneumatic actuator to rapidly apply substantial force to the substrate of the electrode cuff to drive the electrode protrusions into the nerve. Any suitable pneumatic actuator can be used, including those using pistons, expanding chambers, bellows, or any other design.

Swift mechanical force can be applied in a direction collinear, substantially collinear, parallel, or substantially parallel to the length of the substrate and/or electrode protrusion (e.g., in a direction from the proximal end to the distal end of the electrode protrusion). Therefore, swift mechanical force can be applied simultaneously around an electrode cuff to radially force the electrode protrusions into the nerve.

In some cases, the pneumatic actuator can be included in the electrode cuff itself (e.g., coupled to or embedded within the substrate of the electrode cuff). In some cases, the pneumatic actuator can be included in a separable and/or separate tool configured to engage the electrode cuff during implantation. Suitable tools can be configured to temporarily couple to the electrode cuff, surround the electrode cuff, or be placed against the electrode cuff during implantation. For example, a suitable tool can include a pneumatic actuator built into a clamping device designed to clamp the electrode cuff around the nerve. The use of swift mechanical force, such as from a pneumatic actuator, can be combined with mechanical oscillations, such as those described herein.

In some cases, swift mechanical force can be a force applied to the substrate of the electrode cuff to rapidly drive the electrode protrusions into the nerve. The swift mechanical force can be a force applied for a period of time to pierce a depth of the nerve, e.g., the epineurium, without contacting the fascicles. In some cases, an electrical sensor, or any other suitable equipment, can determine the depth of the nerve and apply the swift mechanical force necessary to pierce the epineurium of the nerve.

In some cases, swift mechanical force is a force in a range from 0.5 N to 5 N, e.g., 1 N to 4 N, 2 N to 3 N, or 2.5 N to 3.5 N. In terms of lower thresholds, swift mechanical force is a force greater than 0.5 N, e.g., greater than 0.8 N, greater than 1 N, greater than 1.5 N, greater than 2 N, or greater than 3 N. In some cases, swift mechanical force can be a force less than 5 N, e.g., less than 4 N, less than 3 N, less than 2 N, or less than 1 N. In some cases, the force can be a variable force that is adjusted during implantation of the electrode cuff to drive the electrode(s) through biological structures (e.g., the epineurium).

In some cases, the swift mechanical force is applied for a period of time to penetrate a depth of the epineurium without damaging the fascicles. In some cases, swift mechanical force can be applied for less than 1 s, e.g., less than 800 ms, less than 600 ms, or less than 400 ms. In some cases, swift mechanical force can be applied in a range from 10 ms to 1 s, e.g., from 50 ms to 800 ms, from 100 ms to 600 ms, or from 200 ms to 400 ms. In terms of lower limits, the swift mechanical force can be applied for greater than 10 ms, e.g., greater than 50 ms, greater than 100 ms, or greater than 200 ms.

In some cases, swift mechanical force exerts a force on the substrate to cause the electrode protrusion(s) to penetrate through a depth of the epineurium of the nerve without contacting the fascicles underneath the epineurium. In some cases, the swift mechanical force penetrates a depth from 2

μm to 20 μm of the epineurium, e.g., from 4 μm to 16 μm, from 6 μm to 12 μm, or from 8 μm to 10 μm. In some cases, the swift mechanical force exerts a force on the substrate to cause the electrode protrusion(s) to penetrate through a depth less than 20 μm, e.g., less than 15 μm, less than 10 μm, or less than 5 μm. In terms of lower limits, the swift mechanical force exerts a force on the substrate to cause the electrode protrusion(s) to penetrate through a depth greater than 2 μm, e.g., greater than 5 μm, greater than 10 μm, or greater than 15 μm.

In some cases, swift mechanical force can relate to the amount of force applied to the substrate for a period of time for the distal end(s) of the electrode(s) to completely traverse through a thickness of the epineurium of the nerve. For example, the swift mechanical force can be greater than 0.5 N that is applied for less than 1 s, to penetrate a depth ranging from 2 μm to 20 μm of the nerve.

In some cases, electrode protrusions can be driven into the nerve using any other suitable driving tool, such as linear actuators aligned with a radius of the nerve or actuators designed to otherwise compress the electrode cuff around the nerve. In some cases, the driving tool can apply swift or slow mechanical force to the substrate to cause the protrusions to penetrate the epineurium of the nerve.

A controller can control any of the aforementioned driving tools, such as by sending control signals, controlling the amount of supplied electrical power or supplied pneumatic power, or otherwise. A sensor coupled to the controller can provide dynamic feedback of one or more variables associated with proper installation of the electrode cuff. Examples of suitable variables include pressure or electrical activity. For example, the sensor can measure pressure applied through the protrusions of the electrode cuff to insert the protrusions into the nerve. Higher pressures are expected immediately before the epineurium is pierced, lower pressures are expected within the nerve itself, until slightly higher pressure are seen when the protrusions contact a fascicle. As another example, the sensor can measure electrical activity (e.g., resistance, capacitance, or other electrical activity) at or near the protrusions of the electrode cuff. In some cases, the amount of electrical activity can change in an identifiable pattern before the protrusion contacts the epineurium, during contact with the epineurium, after piercing the epineurium but before contacting the fascicle, and upon contacting the fascicle. In some examples, the controller can detect changes in temperature, such as stopping insertion once temperature has been detected above a threshold. The controller can hold steady or retract the driving tool and/or substrate to avoid over-heating the tissue. In some examples, the controller can guide insertion based on sensing acoustic activity in, at, or near the electrode protrusions. Any number of sensors can be used, including any combination of types of sensors (e.g., pressure and temperature sensors).

In some cases, the controller can provide feedback to a user based on the measurements sensed by the sensor. Feedback can be in the form of visual feedback, such as through a graphical user interface. Examples of such visual feedback can indicate estimated position and/or insertion depth of the electrode protrusions with respect to the neuron. In some cases, feedback can be in the form of tactical feedback. For example, a user may use a tool to help place the electrode cuff, which tool may include an actuator capable of providing tactical feedback to a user holding the tool based on measurements sensed by the sensor, such as when piercing of the epineurium is detected or inferred based on sensor measurements.

The controller can receive measurements of the sensed variable in realtime and use the measurements to control the driving tool. The controller can make a determination of whether or not the protrusion has pierced the epineurium, and thus control how much force to apply through the driving tool and/or when to cease applying force. In some cases, the controller can make a determination of whether or not the protrusion has contacted a fascicle, and thus control insertion of the protrusion to a depth as large as possible without damaging a fascicle.

In some cases, the controller can adjust between driving schemes based on the sensed position of the protrusions. For example, if the controller can make an inference from the measurements from the sensor that the protrusion is outside of the nerve but not in contact with the epineurium, a first driving scheme (e.g., an external placement driving scheme) can be used, such as to slowly bring the protrusion into contact with the epineurium. Upon an inference that the protrusion is in contact with the epineurium, a second driving scheme (e.g., a piercing driving scheme) can be used, such as to increase applied force substantially to pierce the epineurium, possibly immediately followed by a release in the amount of applied force. Upon an inference that the protrusion is within the nerve (e.g., after piercing the epineurium), but not in contact with a fascicle, a third driving scheme (e.g., an internal placement driving scheme) can be used, such as to apply small force suitable for further penetrating the nerve without risk of damaging fascicles. Upon an inference that the protrusion has contacted a fascicle, a fourth driving scheme (e.g., a fascicle contact driving scheme) can be used, such as to either stop driving altogether or apply such force and/or mechanical vibrations capable of displacing the fascicle without damaging the fascicle. Adjustment from one driving scheme to another may include a distinct switch in how the controller operates, or may simply be part of a controller's continuous mode of operation. In other words, there need not be any explicit switch in operating modes.

In some cases, the sensor may undergo a calibration process prior to driving the protrusions into the nerve. The calibration process may occur after the electrode cuff has been placed around the nerve, but before the protrusions have been driven into the nerve. The calibration process can include taking measurements, such as measurements of electrical activity, when the protrusions are positioned adjacent to and/or in contact with the epineurium. The calibration process can generate a baseline usable by the controller when making inferences or determinations based on subsequent sensor data. In some cases, the calibration process can act to offset or normalize incoming sensor data, and the controller can make inferences or determinations based on the normalized data.

The number of sensors and resolution of driving mechanisms can be small (e.g., one) or large (e.g., many). For example, a single pressure sensor and/or a single actuator of a driving tool can be used to provide sufficient dynamic feedback for automated or semi-automated installation of the electrode cuff on a nerve. In some cases, however, multiple sensors can be used to provide higher resolution (e.g., more granularity) in sensing across the circumference of the electrode cuff. In some cases, with or without multiple sensors, multiple driving mechanisms can be used to provide higher resolution (e.g., more granularity) in driving force across the circumference of the electrode cuff. For example, mechanical actuators moving in parallel with a first radius of the nerve can operate with different force than mechanical actuators moving in parallel with a second radius of the nerve. In this fashion, it may be the case that protrusions in one region of the electrode cuff can be driven separately from protrusions in another region of the electrode cuff, thus providing improved placement of more protrusions during installation.

In some cases, a combination of different types of sensors can be used. For example, pressure sensors and electrical sensors can be used in conjunction with one another to provide feedback to the controller. The controller can make an inference or determination based on one or more of the received signals.

In some cases, upon inferring or detecting piercing of the epineurium of a nerve bundle, the controller can switch from a first set of parameters to a second set of parameters. The switch from a first set of parameters to a second set of parameters can include a change in sensor used, combination of sensors used, variables associated with any sensor(s) used, or other changes with respect to how measurements are sensed. For example, prior to piercing the epineurium, the controller can monitor or primarily monitor pressure, temperature, and/or acoustic activity to dynamically control displacement of the driving tool. After piercing of the epineurium is detected or inferred, the controller can switch to monitoring or primarily monitoring electrical activity, such as electrical activity between electrodes within the nerve bundle.

In some cases, the present disclosure provides a method of applying an electrode cuff to target tissue. The method comprises: providing an electrode cuff comprising a substrate and at least one protrusion having one or more electrodes thereon and extending from a tissue-facing surface of the substrate; positioning the tissue-facing surface of the substrate against a nerve; and actuating a driving tool to apply mechanical energy to the electrode cuff to facilitate piercing the at least one protrusion into the nerve, wherein actuating the driving tool comprises: measuring an insertion-indicative value, the insertion-indicative value being indicative of whether the at least one electrode protrusion has penetrated at least part of the nerve; wherein actuating the driving tool further comprises dynamically controlling the mechanical force applied to the substrate in response to the measured insertion-indicative value.

In some cases, measuring the insertion-indicative value includes detecting electrical activity passing through at least one of the one or more individual electrodes. In some cases, measuring the insertion-indicative value includes detecting electrical activity passing through the one or more individual electrodes of at least two of the at least one electrode protrusion. In some cases, measuring the insertion-indicative value includes detecting electrical activity passing through at least two of the one or more individual electrodes of one of the at least one electrode protrusion. In some cases, measuring the insertion-indicative value includes measuring force applied by the driving tool. In some cases, the driving tool includes at least one pneumatic actuator, and wherein measuring the insertion-indicative value includes measuring pneumatic pressure applied to the at least one pneumatic actuator.

In some cases, measuring the insertion-indicative value includes detecting acoustic activity generated when one or more of the electrode protrusions is pushed by the driving tool through tissue, such as a tissue layer or one or more different tissue layers.

In some cases, measuring the insertion-indicative value includes detecting temperature change generated due to any heat produced at the electrode-tissue interface when one or more of the electrode protrusions is pushed by the driving tool through tissue, such as a tissue layer or one or more different tissue layers.

Certain aspects and features of the present disclosure can improve electrode placement within a nerve. The electrodes can be located within the nerve without damaging fascicles within the nerve and without subjecting the nerve to substantial deformation (e.g., without flattening the nerve). As such, the electrode cuff can provide improved electrical conductivity between the electrodes and nerves within the nerve. The improved electrical conductivity can improve the ability for stimuli to be transmitted to the nerves and can improve the ability to receive strong signals from the nerves. Employing certain aspects and features of the present disclosure, a medical device can receive electrical signals from nerves at a relatively high signal-to-noise ratio, at least as compared to traditional peripheral nerve electrodes. Further, the improved signal-to-noise ratio can enable additional features previously unavailable or impractical, such as closed loop feedback systems taking advantage of peripheral neural activity sensed using an electrode cuff implantation as described herein. Further, certain aspects and features of the present disclosure can be especially useful for neuromodulation implantable devices.

These illustrative examples are given to introduce the reader to the general subject matter discussed here and are not intended to limit the scope of the disclosed concepts. The following sections describe various additional features and examples with reference to the drawings in which like numerals indicate like elements, and directional descriptions are used to describe the illustrative embodiments but, like the illustrative embodiments, should not be used to limit the present disclosure. The elements included in the illustrations herein may not be drawn to scale.

FIG. 1 is a schematic diagram of an electrode placement system 100 securing an electrode cuff 104 to a nerve 102 according to certain aspects of the present disclosure. The electrode placement system 100 can include an electrode cuff 104 and a driving tool 106. The electrode cuff 104 can include one or more electrodes disposed within the nerve 102 when the electrode cuff 104 is implanted. The electrodes can be coupled to a controller 112 through an electrical connection 110. The controller 112 can be any suitable piece of electrical equipment for driving or receiving current through the electrodes. For example, a controller 112 can be a pulse generator, an electrical sensor, or any other suitable equipment. The controller 112 can be located distant from the electrode cuff 104, can be located adjacent the electrode cuff 104, or can be integrated into the electrode cuff 104.

The driving tool 106 is used to drive the electrode protrusions of the electrode cuff 104 into the nerve 102. As depicted in FIG. 1, the driving tool 106 is separable from the electrode cuff 104, and thus removable after implantation of the electrode cuff 104 is complete. However, in some cases, the driving tool 106 can be integrated into the electrode cuff 104 itself and can remain after implantation of the electrode cuff 104 is complete. During implantation using a driving tool 106 that is separable from the electrode cuff 104, the driving tool 106 can be manually held against the electrode cuff 104 (e.g., via manual manipulation of a tool), temporarily secured against the electrode cuff 104 (e.g., via a clamp), or temporarily coupled to the electrode cuff 104 (e.g., via interlocking fittings of the driving tool 106 and electrode cuff 104). The driving tool 106 can take many forms. For example, a driving tool 106 can be integrated into a small cuff deployable about the electrode cuff 104 during implantation. As another example, the driving tool 106 can be integrated into a laparoscopic tool designed to contact or apply pressure to the electrode cuff 104, with one or more drivers 108 located at a distal end of the laparoscopic tool.

The driving tool 106 can include one or more drivers 108. As depicted in FIG. 1, the driving tool 106 includes two drivers 108 located opposite the nerve 102 from one another. In some cases, a plurality of drivers 108 can be located equidistant about the circumference of the nerve 102 or electrode cuff 104. A driver 108 can be any suitable device for generating mechanical oscillations in the electrode cuff 104 or swift mechanical force rapidly displacing the electrode protrusions (e.g., from the force applied to the substrate of the electrode cuff) of the electrode cuff 104 into the nerve 102. Examples of suitable drivers 108 include mechanical transducers (e.g., ultrasonic transducers) or pneumatic drivers (e.g., pneumatic actuators). In some cases, a driving tool 106 can include a combination of mechanical transducers and pneumatic drivers.

In an example, a driving tool 106 having mechanical transducers as drivers 108 can include one or more drivers 108 operatively coupled to induce mechanical oscillations in the electrode cuff 104. In this example, the mechanical transducers can be secured against the outside surface of the electrode cuff 104, such as through compression. Other mechanical transducers and driving tool designs can be used.

In another example, a driving tool 106 having pneumatic drivers as the drivers 108 can include pneumatic pistons or pneumatic bellows designed to rapidly expand in size when supplied with compressed air. For example, the driving tool 106 can include a rigid outer wall and a flexible inner wall defining a chamber into which compressed air can be supplied, which can cause the flexible inner wall to rapidly decrease in its inner diameter, thus applying swift mechanical force to the electrode cuff 104 to drive its electrodes into the nerve. Other pneumatic drivers and driving tool designs can be used.

The drivers 108 of the driving tool 106 can be coupled to a power source 116 through a supply line 114. The power source 116 and supply line 114 can be selected based on the type of drivers 108 used. When a mechanical transducer is used, the power source 116 can include a source of electrical power and the supply line 114 can include a conductor (e.g., electrical wire). When a pneumatic driver is used, the power source 116 can include a source of pressurized fluid or compressed fluid, such as compressed gas or compressed air, and the supply line 114 can include a hollow tube suitable for delivering the fluid under pressure. In some cases, the power source 116 can be located distant from the drivers 108, such as external to the patient in which the electrode cuff 104 is being implanted. In some cases, one or more power sources 116 can be integrated into the driving tool 106. For example, a battery or capacitor can be integrated into the driving tool 106 to power an electrically operated driver 108, or a chamber of compressed air can be integrated into the driving tool 106 to power a pneumatically operated driver 108.

In some cases, the components of the electrode placement system 100 can be supplied bundled together (e.g., a kit). The electrode placement system 100 can include additional components related to the electrode cuff 104 and driving tool 106, such as controller 112, power source 116, and any suitable supply lines 114 or electrical connections 110. However, in some cases, the components of the electrode placement system 100 can be provided individually and simply used together for implantation of the electrode cuff 104.

Figure 2:
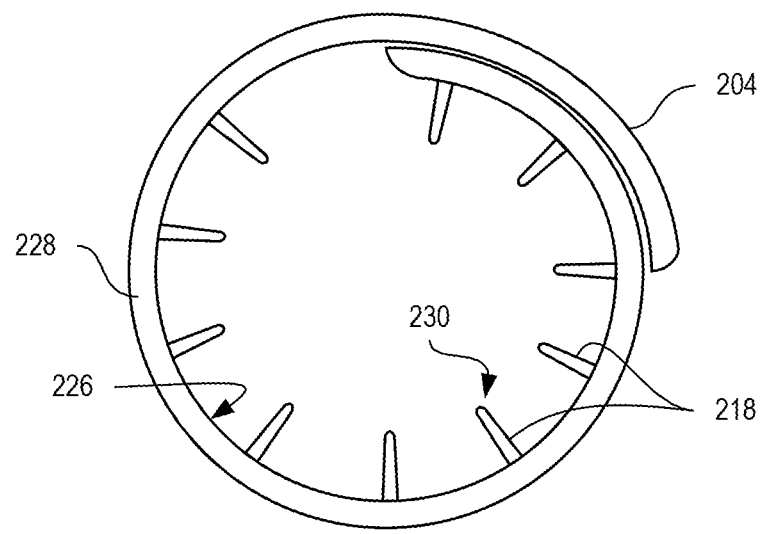
FIG. 2 is an end view of an electrode cuff wrappable about a nerve according to certain aspects of the present disclosure.

FIG. 2 is an end view of an electrode cuff 204 wrappable about a nerve according to certain aspects of the present disclosure. The electrode cuff 204 can be similar to the electrode cuff 104 of FIG. 1. The electrode cuff 204 can include a substrate 228 capable of wrapping around a nerve. The substrate 228 can have sufficient dimensions to wrap over itself by a portion when implanted on a nerve. The substrate 228 can include a tissue-facing surface 226. The tissue-facing surface 226 can be located opposite an outer surface. The tissue-facing surface 226 can naturally have a concave shape, such as the inside of a cylinder, which can be designed to match the geometry of the nerve to which it will be implanted. The electrode cuff 204 can be made of a material capable of flexing such that the substrate 228 can be at least partially unwrapped (e.g., flattened) to allow a nerve to be placed within the inner diameter of the electrode cuff 204. In some cases, the electrode cuff 204 has a natural bias to return towards a cylindrical or partially cylindrical shape, such as the shape depicted in FIG. 2. Thus, after opening the electrode cuff 204 to fit the nerve inside, releasing the electrode cuff 204 can cause it to wrap around the nerve and return to the shape depicted in FIG. 2.

The tissue-facing surface 226 can include one or more electrode protrusions 218. The electrode protrusions 218 can extend from the tissue-facing surface 226 by a distance. The electrode protrusions 218 can extend in a radial direction, towards a center of the electrode cuff 204. The electrode protrusions 218 can take any suitable shape or orientation. In some cases, multiple electrode protrusions 218 are circumferentially spaced apart from one another. For example, as depicted in FIG. 2, several electrode protrusions 218 are located approximately equidistant around the tissue-facing surface 226, although that need not be the case. In some cases, multiple electrode protrusions 218 are longitudinally (e.g., along a direction into the page as seen in FIG. 2) spaced apart from one another.

Each electrode protrusion 218 can have a distal end 230. Each distal end 230 can have a blunt shape (e.g., not pointed or not sharp). The blunt shape can be a rounded shape.

Figure 3:
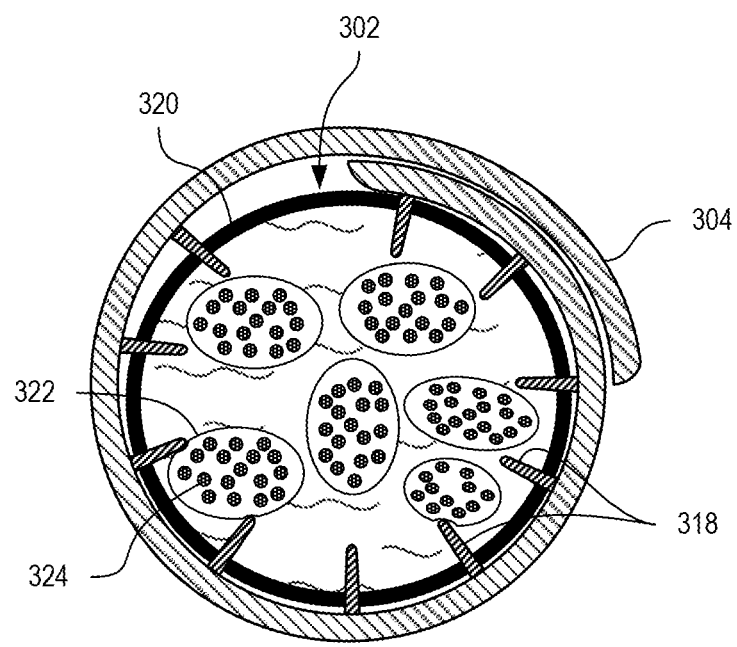
FIG. 3 is a partial cutaway end view of an electrode cuff wrapped about a nerve according to certain aspects of the present disclosure.

FIG. 3 is a partial cutaway end view of an electrode cuff 304 wrapped about a nerve 302 according to certain aspects of the present disclosure. Electrode cuff 304 can be similar to electrode cuff 204 after it has been implanted about a nerve 302. Electrode cuff 304 was implanted about nerve 302 as described in further detail herein, such as using a driving tool (e.g., driving tool 106 of FIG. 1).

When the electrode cuff 304 is implanted about a nerve 302, the electrode protrusions 318 can pierce the epineurium 320 of the nerve 302. Due to the blunt shape of the distal ends of the electrode protrusions 318 and the implantation technique, the electrode protrusions 318 do not rupture or damage the fascicles 332 or the neurons 324 therein. If an electrode protrusion 318 contacts a fascicle 332, the blunt end can displace the fascicle 322 itself or the perineurium around the fascicle 332. When mechanical oscillations are used, the oscillations can displace the fascicle 322 or its perineurium.

In some cases, the electrode protrusions 318 can be sized to extend into the nerve 302 to a depth designed to prevent damage to fascicle 332.

Figure 4:
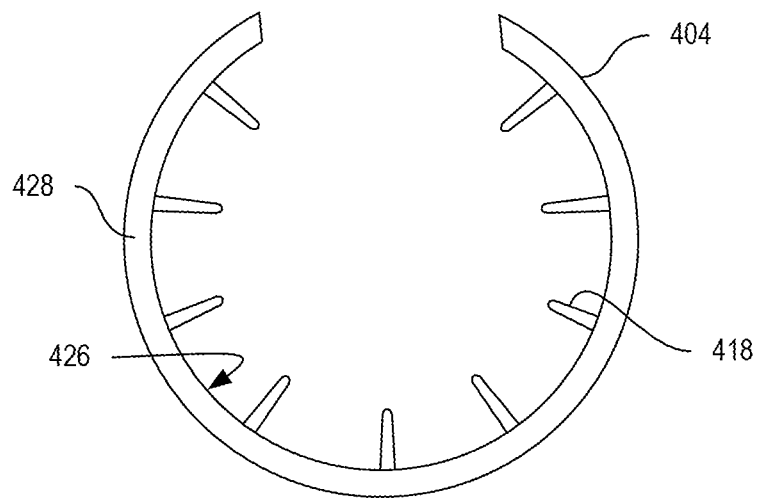
FIG. 4 is an end view of an electrode cuff partially encirclable about a nerve according to certain aspects of the present disclosure.

FIG. 4 is an end view of an electrode cuff 404 partially encirclable about a nerve according to certain aspects of the present disclosure. Electrode cuff 404 can be similar to electrode cuff 204 of FIG. 2, however with a substrate 428 that does not entirely encircle the nerve. Thus, a gap remains between ends of the substrate 428, which can be flexed open to accept a nerve during implantation. The substrate still includes a tissue-facing surface 426 having one or more electrode protrusions 418 extending therefrom.

Figure 5:
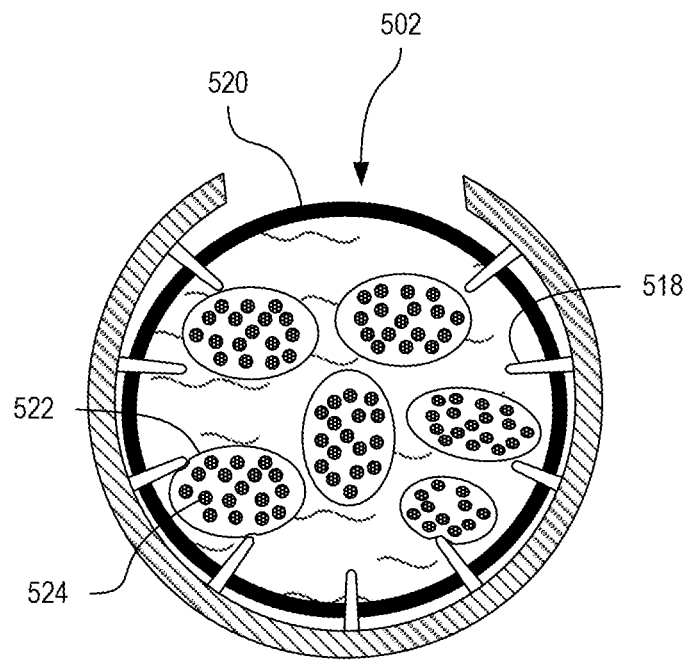
FIG. 5 is a partial cutaway end view of an electrode cuff partially encircled about a nerve according to certain aspects of the present disclosure.

FIG. 5 is a partial cutaway end view of an electrode cuff 504 partially encircled about a nerve 502 according to certain aspects of the present disclosure. Electrode cuff 504 can be similar to electrode cuff 404 of FIG. 4 after it has been implanted about a nerve 502. Electrode cuff 504 was implanted about nerve 502 as described in further detail herein, such as using a driving tool (e.g., driving tool 106 of FIG. 1).

When the electrode cuff 504 is implanted about a nerve 502, the electrode protrusions 518 can pierce the epineurium 520 of the nerve 502. Due to the blunt shape of the distal ends of the electrode protrusions 518 and the implantation technique, the electrode protrusions 518 do not rupture or damage the fascicles 552 or the neurons 524 therein.

Figure 6:
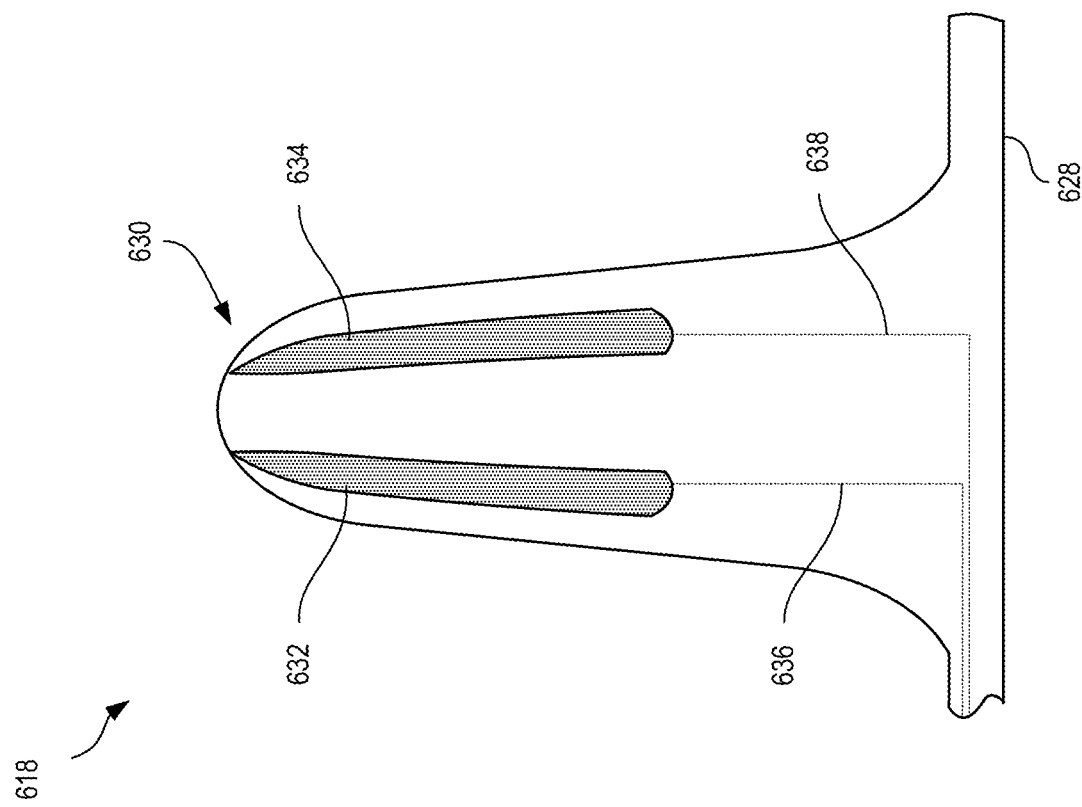
FIG. 6 is a close-up view depicting a portion of a multi-electrode protrusion of an electrode cuff according to certain aspects of the present disclosure.

FIG. 6 is a close-up view depicting a portion of a multi-electrode protrusion 618 of an electrode cuff according to certain aspects of the present disclosure. Protrusion 618 can be similar to electrode protrusions 218 of FIG. 2. The protrusion 618 can extend from and be formed of the same material as the substrate 628, although that need not be the case. The protrusion 618 can have a distal end 630 that is relatively blunt in shape. The protrusion 618 can include multiple electrodes 632, 634. As depicted in FIG. 6, each electrode 632, 634 is individually addressable via respective wires 636, 638. However, in some cases, a single protrusion 618 can include multiple electrodes that are electrically shorted to one another through a common wire. Electrodes 632, 634 can be plated to, adhered to, or otherwise coupled to the surface of the protrusion 618. In some cases, electrodes 632, 634 can be embedded within the body of the protrusion 618. Wires 636, 638 can be located external to or within the body of the protrusion 618 and/or the substrate 628.

Figure 7:
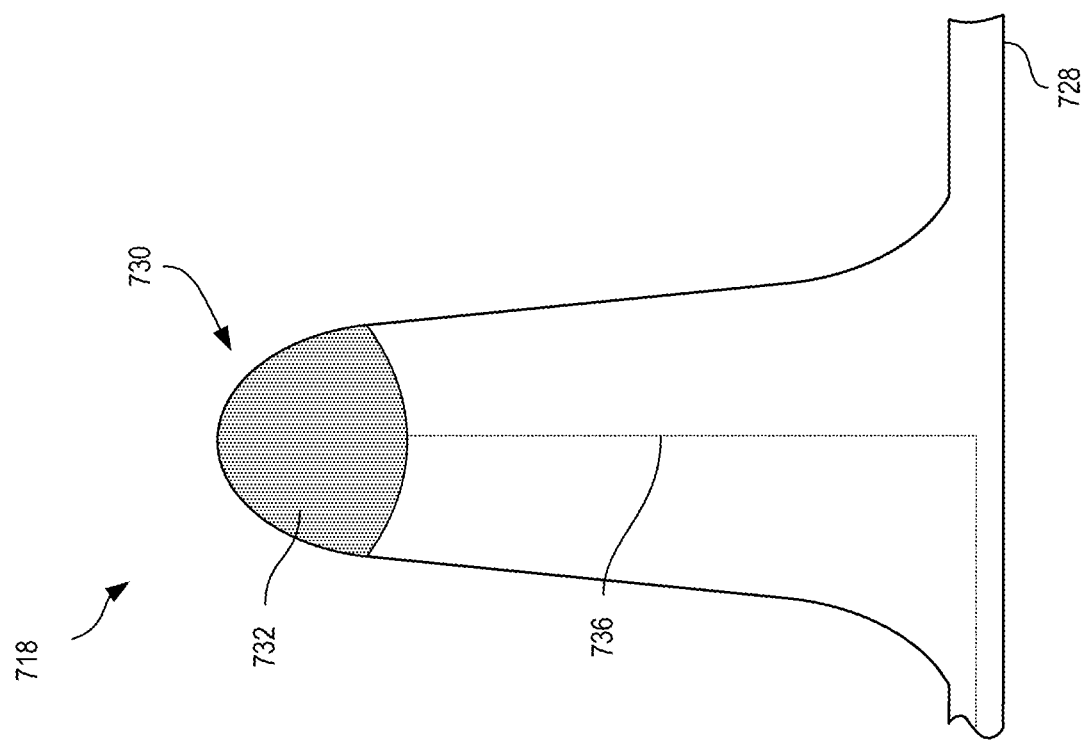
FIG. 7 is a close-up view depicting a portion of a single-electrode protrusion of an electrode cuff according to certain aspects of the present disclosure.

FIG. 7 is a close-up view depicting a portion of a single-electrode protrusion 718 of an electrode cuff according to certain aspects of the present disclosure. Protrusion 718 can be similar to electrode protrusions 218 of FIG. 2. The protrusion 718 can extend from and be formed of the same material as the substrate 728, although that need not be the case. The protrusion 718 can have a distal end 730 that is relatively blunt in shape. The protrusion 718 can include a single electrodes 732. As depicted in FIG. 7, the electrode 732 is located at the distal end 730 of the protrusion 718, however that need not be the case. Electrode 732 can be coupled to a wire 736 for carrying electrical current. Electrode 732 can be plated to, adhered to, or otherwise coupled to the surface of the protrusion 718. In some cases, electrode 732 can be embedded within the body of the protrusion 718. Wire 736 can be located external to or within the body of the protrusion 718 and/or the substrate 728.

Figure 8:
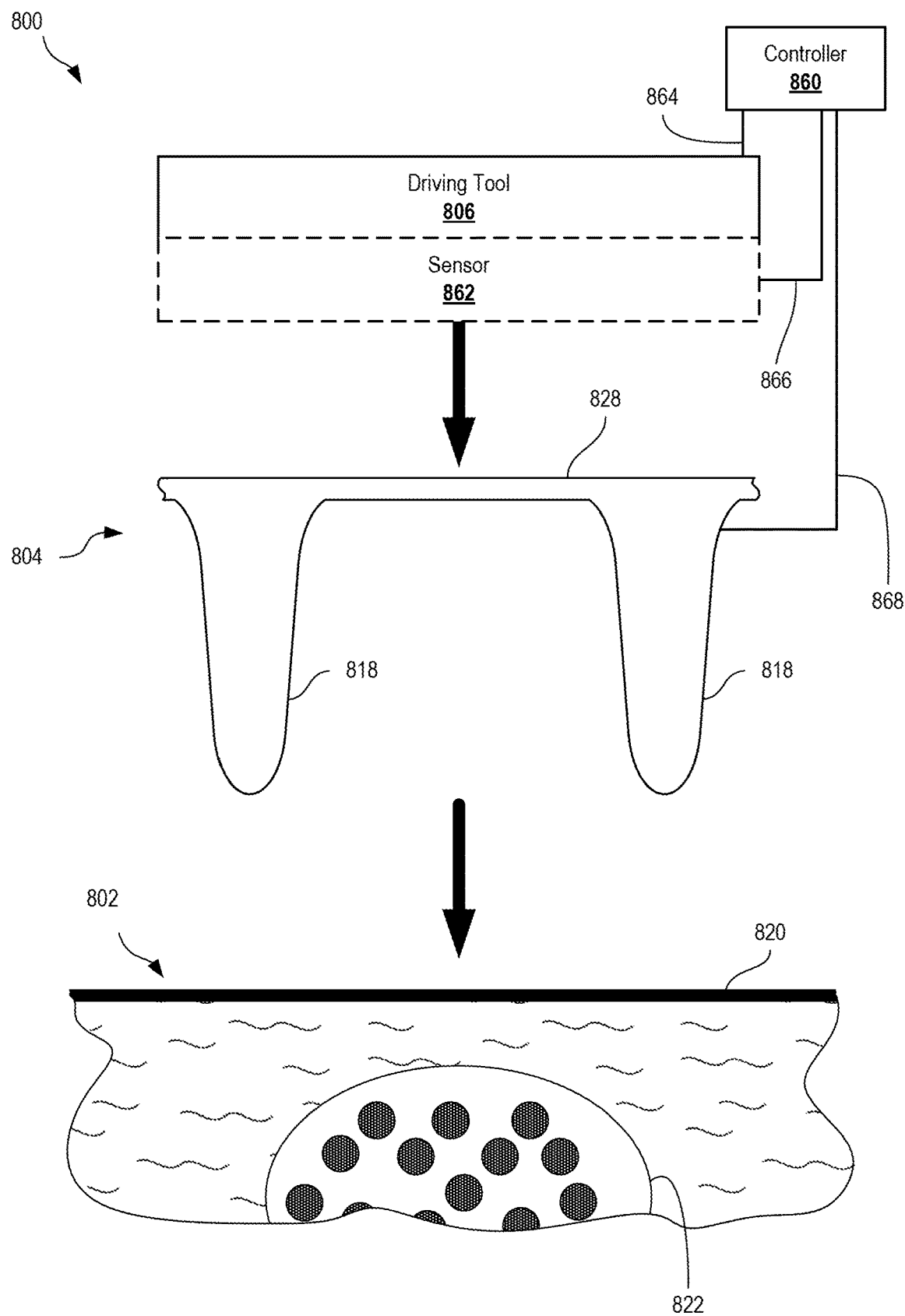
FIG. 8 is a schematic diagram depicting an electrode placement system for securing an electrode cuff to a nerve according to certain aspects of the present disclosure.

FIG. 8 is a schematic diagram depicting an electrode placement system 800 for securing an electrode cuff 804 to a nerve 802 according to certain aspects of the present disclosure. The electrode placement system 800 can include a driving tool 806 and an electrode cuff 804. The electrode cuff 804 can include a substrate 828 and one or more electrode protrusions 818. The components of electrode placement system 800 can be similar to the electrode cuff 104 and driving tool 106 of FIG. 1.

The electrode placement system 800 can be used to secure the electrode cuff 804 against the nerve 802 by piercing the epineurium 820 with the electrode protrusions 818 without damaging the fascicle 822.

Sensor 862 can be used in conjunction with a controller 860 to control actuation of the driving tool 806. Sensor 862 can be positioned in any suitable location, including between the driving tool 806 and the substrate 828. However, in some cases, sensor 862 can be incorporated into the substrate 828, the electrode protrusions 818, the driving tool 806, and/or the controller 860.

The sensor 862 can be any sensor suitable for measuring a variable insertion-indicative value of insertion of the electrode protrusions 818 into the nerve 802. For example, sensor 862 can be a pressure sensor designed to measure the amount of pressure applied from the driving tool 806, through the electrode protrusions 818. In such cases, the sensor 862 could sense relatively high pressures immediately before piercing the epineurium 820, sense relatively low pressures immediately after piercing the epineurium 820, and sense slightly higher pressure upon contact with a fascicle 822. The controller 860 can thus use the sensed pressure to control the driving tool 806 to stop applying pressure after piercing the epineurium 820 and before damaging the fascicle 822.

As another example, sensor 862 can be an electrical sensor designed to detect electrical activity across one or more sensing electrodes. The sensing electrodes can include electrodes of the electrode protrusions 818 (e.g., electrodes 632, 634 of FIG. 6 or electrode 732 of FIG. 7) and/or additional electrodes separate from the electrodes of the electrode protrusions 818. In such cases, the sensor 862 may be a resistance or capacitance sensor for measuring resistance or capacitance adjacent the sensing electrodes. For example, the sensor 862 may detect a first resistance while the electrode protrusions 818 remain outside of the nerve 802, a second resistance upon contact with the epineurium 820, a third resistance upon piercing the epineurium 820 and entering the nerve 802, and a fourth resistance upon contacting the fascicle 822. The controller 860 can thus use the sensed electrical activity to control the driving tool 806 to stop applying pressure after piercing the epineurium 820 and before damaging the fascicle 822.

The sensor 862 can be coupled to the controller 860 by one or more sensor links 866. The sensor link 866 can be any suitable connection for conveying sensed information to the controller 860, such as an electrical connection, a wireless connection, or fluid connection (e.g., a pressure line). The driving tool 806 can be coupled to the controller 860 by one or more driving links 864. The driving link 864 can be any suitable connection for sending signals and/or power to control the driving tool 806, such as an electrical connection, a wireless connection, or fluid connection (e.g., a pressure line). The electrodes of the electrode cuff 804 can be coupled to the controller 860 by one or more electrode links 868. The electrode link 868 can be any suitable connection for conveying electrical signals sensed by the electrodes 868 to the controller 860, such as an electrical connection, a wireless connection, or fluid connection (e.g., a pressure line). In some cases, sensor 862 can be incorporated into the driving tool 806, in which case the driving link 864 can also act as a sensor link 866. In some cases, the sensor 862 can include one or more electrodes of the electrode cuff 804, in which case the electrode link 868 can act as part or all of the sensor link 866.

Figure 9:
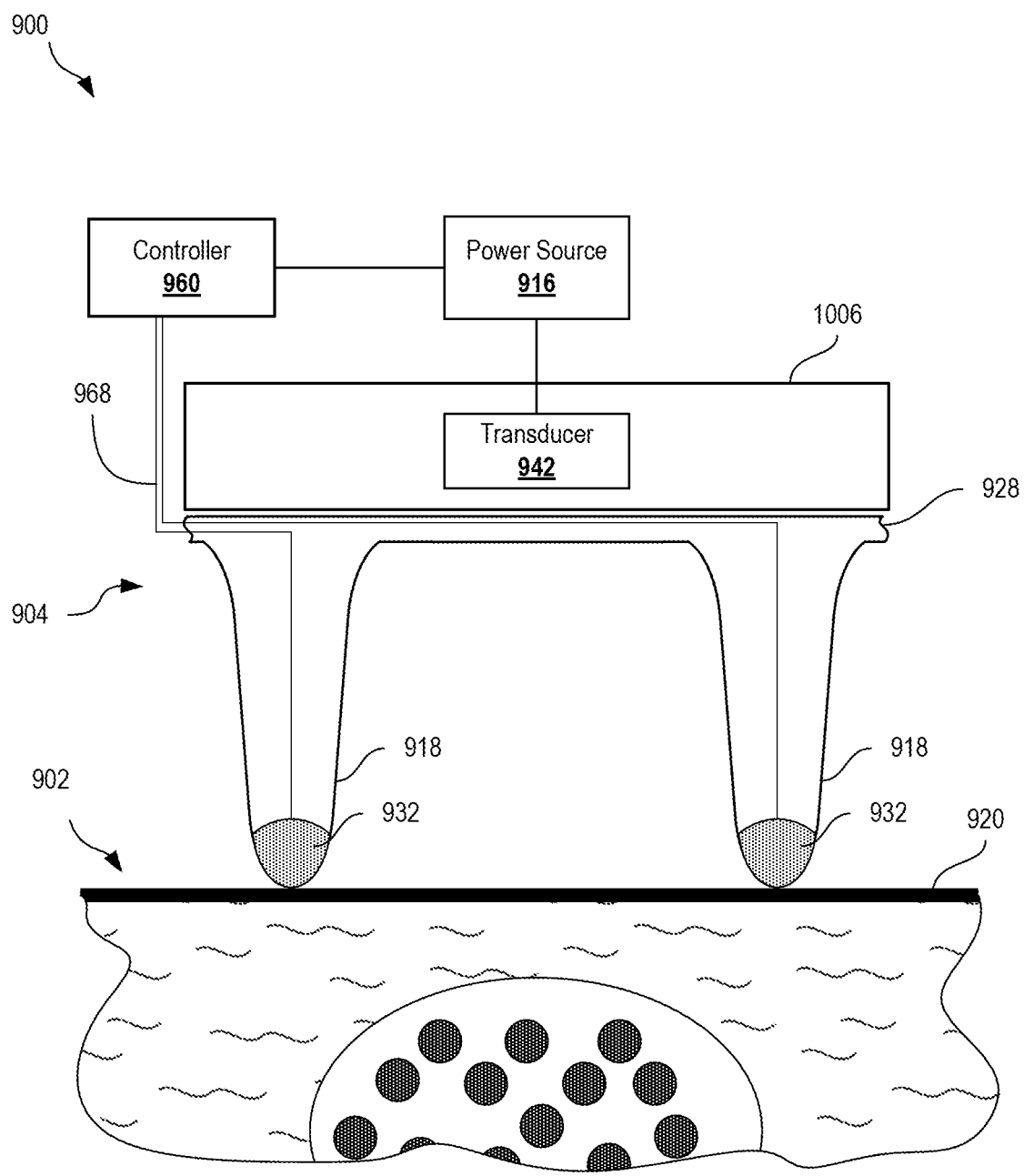
FIG. 9 is a schematic diagram depicting placement of an oscillation-driven electrode cuff against a nerve according to certain aspects of the present disclosure.

FIG. 9 is a schematic diagram depicting placement of an oscillation-driven electrode cuff 904 against a nerve 902 according to certain aspects of the present disclosure. An electrode placement system 900 can be similar to electrode placement system 800 of FIG. 8. Electrode placement system 900 can include a driving tool 906 and an electrode cuff 904.

The driving tool 906 can include a transducer 942 coupled to a power source 916. The transducer 942 can be any suitable mechanical transducer or mechanical oscillator, such as an ultrasonic transducer.

During a pre-insertion stage of implantation, the electrode cuff 904 can be placed adjacent the nerve 902 such that the electrode protrusions 918 can contact the epineurium 920. The driving tool 906 can be placed against the substrate 928 of the electrode cuff 904.

A controller 960 may be coupled to electrodes 932 of electrode protrusions 918 by an electrode link 968. The electrodes 932 of the electrode protrusions 918 may be in contact with the epineurium 920, allowing the controller 960 to measure electrical activity between the electrodes 932 associated with being in contact with the epineurium 920. Optionally, calibration can take place in this pre-insertion stage. The controller 960 can be coupled to the power source 916 to begin initial insertion, as depicted in FIG. 10.

Figure 10:
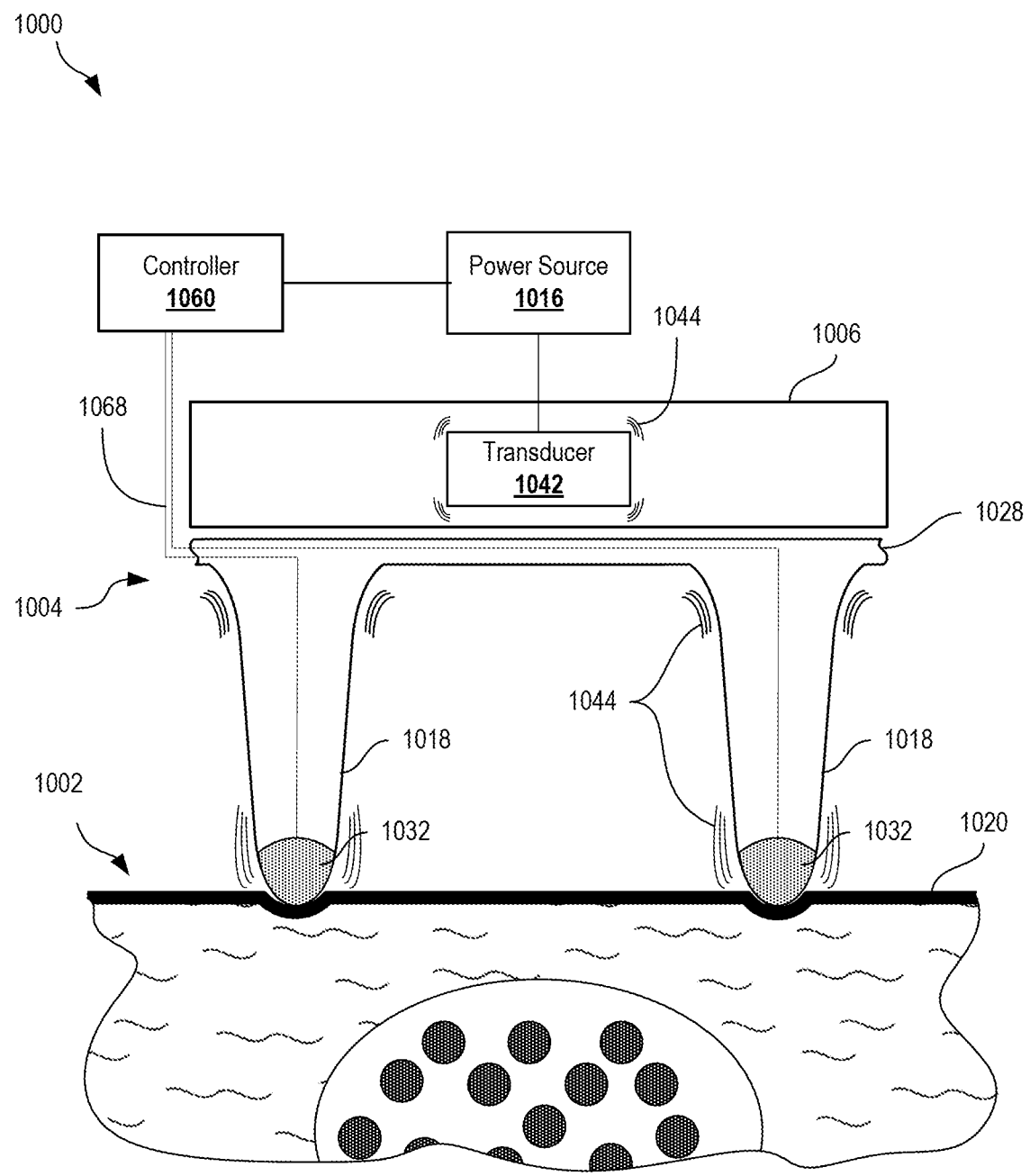
FIG. 10 is a schematic diagram depicting initial insertion of an oscillation-driven electrode cuff into a nerve according to certain aspects of the present disclosure.

FIG. 10 is a schematic diagram depicting initial insertion of an oscillation-driven electrode cuff 1004 into a nerve 1002 according to certain aspects of the present disclosure. An electrode placement system 1000 can be similar to electrode placement system 900 of FIG. 9 when the insertion portion of implantation is underway.

During an insertion portion of implantation, power from power supply 1016 can be fed into transducer 1042 within the driving tool 1006 to initiate oscillations 1044 (e.g., vibrations). Oscillations 1044 can be induced in the electrode cuff 1004, such as at the electrode protrusions 1018. In some cases, oscillations 1044 can be transmitted through mechanical coupling between the driving tool 1006 and the substrate 1028 of the electrode cuff 1004. For example, pressure can be applied to urge the driving tool 1006 towards the substrate 1028. Oscillations 1044 can insert the electrode protrusions 1018 through the epineurium 1020 of the nerve 1002.

A controller 1060 may be coupled to electrodes 1032 of electrode protrusions 1018 by an electrode link 1068. The electrodes 1032 of the electrode protrusions 1018 may be displacing the epineurium 1020, providing more contact area between the electrodes 1032 and the epineurium 1020. The controller 1060 can measure electrical activity between the electrodes 1032 associated with being an initial insertion stage, where the epineurium 1020 has not been pierced, but is being displaced by the protrusions 1018. The controller 1060 can be coupled to the power source 1016 to further control insertion, such as increasing oscillation speed.

Figure 11:
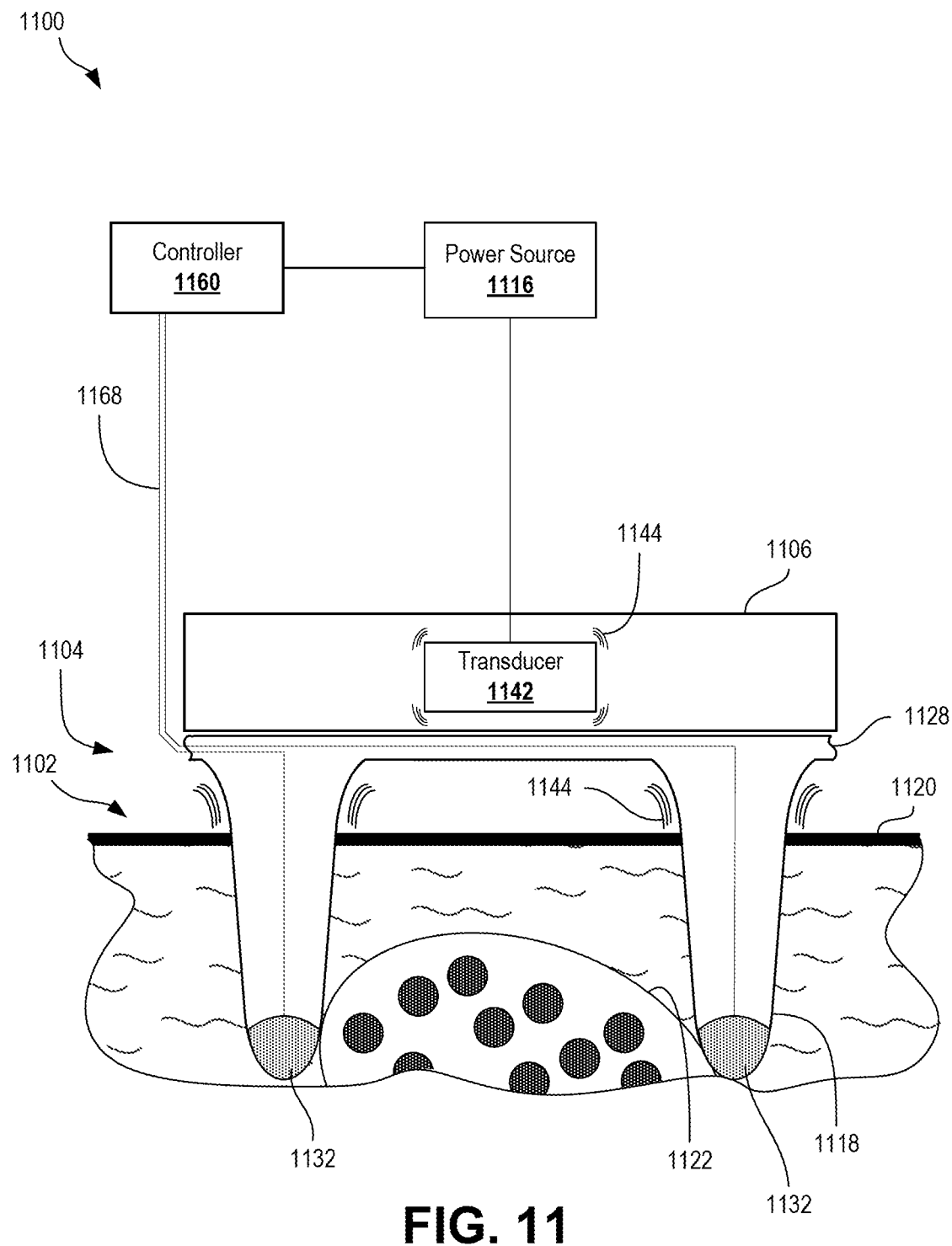
FIG. 11 is a schematic diagram depicting insertion of an oscillation-driven electrode cuff into a nerve according to certain aspects of the present disclosure.

FIG. 11 is a schematic diagram depicting insertion of an oscillation-driven electrode cuff 1104 into a nerve 1102 according to certain aspects of the present disclosure. An electrode placement system 1100 can be similar to electrode placement system 1000 of FIG. 10 after continued insertion of the electrode protrusions 1118 into the nerve 1102.

The power source 1116 can power the transducer 1142 to induce oscillations 1144 in the electrode cuff 1104. Pressure can be applied (e.g., through the driving tool 1106 and the substrate 1128) to urge the electrode protrusions 1118 into the nerve 1102. The oscillations 1144 insert the electrode protrusions 1118 through the epineurium 1120 and into the nerve 1102. Additionally, the oscillations 1144 can reduce the likelihood that the electrode protrusions 1118 would damage a fascicle 1122. For example, oscillations 1144 may move the fascicle 1122 rather than puncturing of its perineurium. As described above, in some cases, the electrode protrusions 1118 can have a length that is shorter than the depth of a fascicle 1122, allowing the electrodes of the electrode protrusions 1118 to be placed within the nerve 1102 and adjacent fascicles 1122 while minimizing risk of damage to fascicles 1122 during implantation of the electrode cuff 1102.

A controller 1160 may be coupled to electrodes 1132 of electrode protrusions 1118 by an electrode link 1168. The electrodes 1132 of the electrode protrusions 1118 may be within the nerve and may or may not be in contact with the fascicle 1122. The controller 1160 can measure electrical activity between the electrodes 1132. The measured electrical activity can be characteristic of or associated with electrodes 1132 being within the nerve 1102 and/or electrodes 1132 being in contact with a fascicle 1122. In response to this measured electrical activity, the controller 1160 can control the power source 1116 to prevent damage to the fascicle, such as decreasing or halting oscillations, decreasing or halting insertion force, and/or any other adjustments suitable to decrease risk of damaging fascicles while maintaining a desirable insertion depth of the protrusion 1118.

Figure 12:
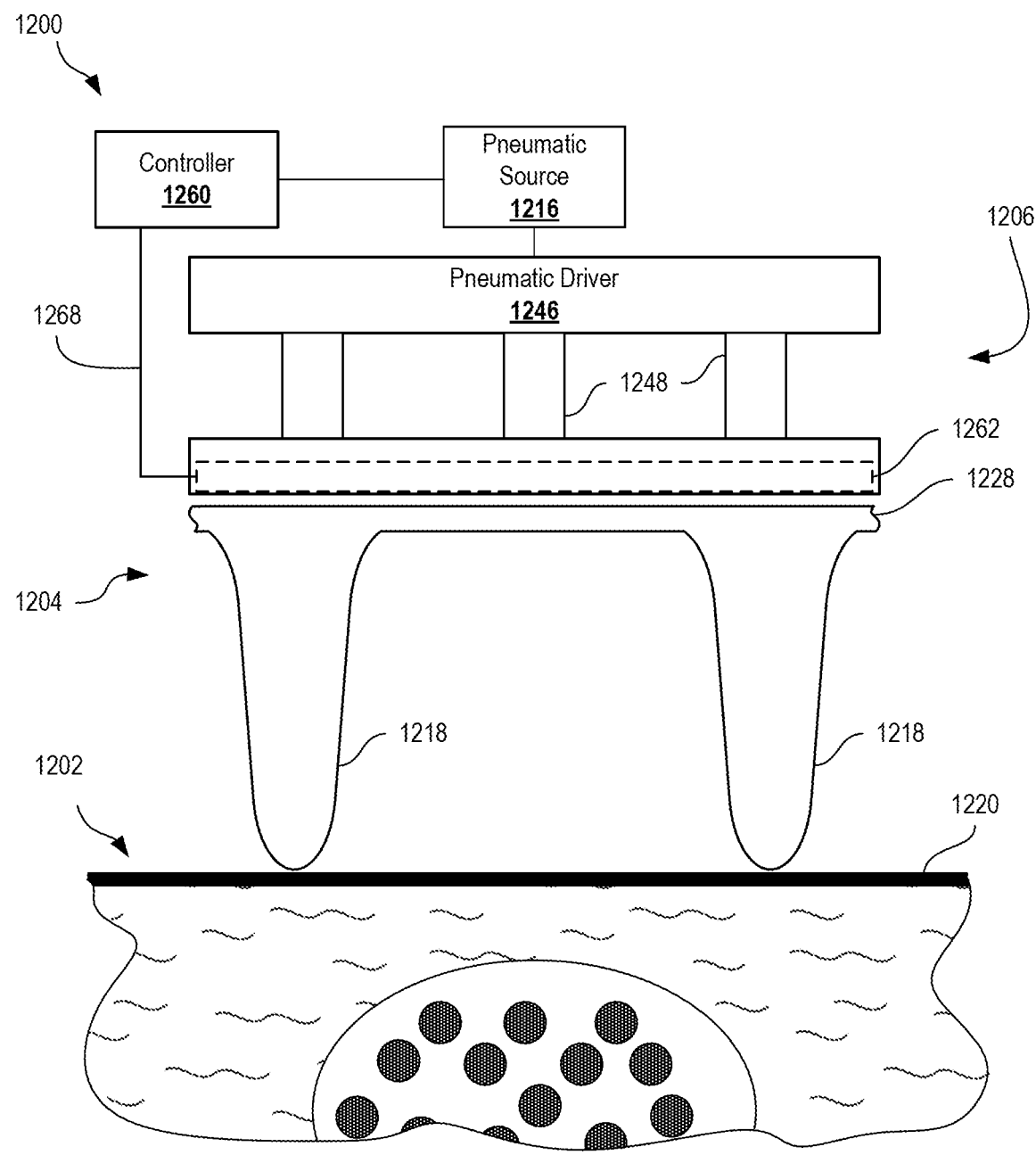
FIG. 12 is a schematic diagram depicting placement of a pneumatic-driven electrode cuff against a nerve according to certain aspects of the present disclosure.

FIG. 12 is a schematic diagram depicting placement of a pneumatic-driven electrode cuff 1204 against a nerve 1202 according to certain aspects of the present disclosure. An electrode placement system 1200 can be similar to electrode placement system 800 of FIG. 8. Electrode placement system 1200 can include a driving tool 1206 and an electrode cuff 1204.

The driving tool 1206 can include a pneumatic driver 1246 coupled to a power source that is a pneumatic source 1216 (e.g., source of compressed air). The pneumatic driver 1246 depicted in FIGS. 12-14 is shown schematically as having pistons 1248, although the pneumatic driver 1246 can take other suitable forms, including expanding chambers, bellows, or other pneumatic actuators.

During a pre-insertion stage of implantation, the electrode cuff 1204 can be positioned adjacent the nerve 1202 such that the electrode protrusions 1218 can contact the epineurium 1220. The driving tool 1206 can be positioned against the substrate 1228 of the electrode cuff 1204.

A controller 1260 may be coupled to a pressure sensor 1262 positioned to measure force between the pneumatic driver 1246 and the electrode protrusions 1218. The electrode protrusions 1218 may be in contact with the epineurium 1220. Optionally, calibration can take place in this pre-insertion stage to measure a baseline pressure between the pneumatic driver 1246 and the epineurium 1220, and thus the pressure being applied through the electrode protrusions 1218. The controller 1260 can be coupled to the pneumatic source 1216 to control initial insertion, as depicted in FIG. 13.

Figure 13:
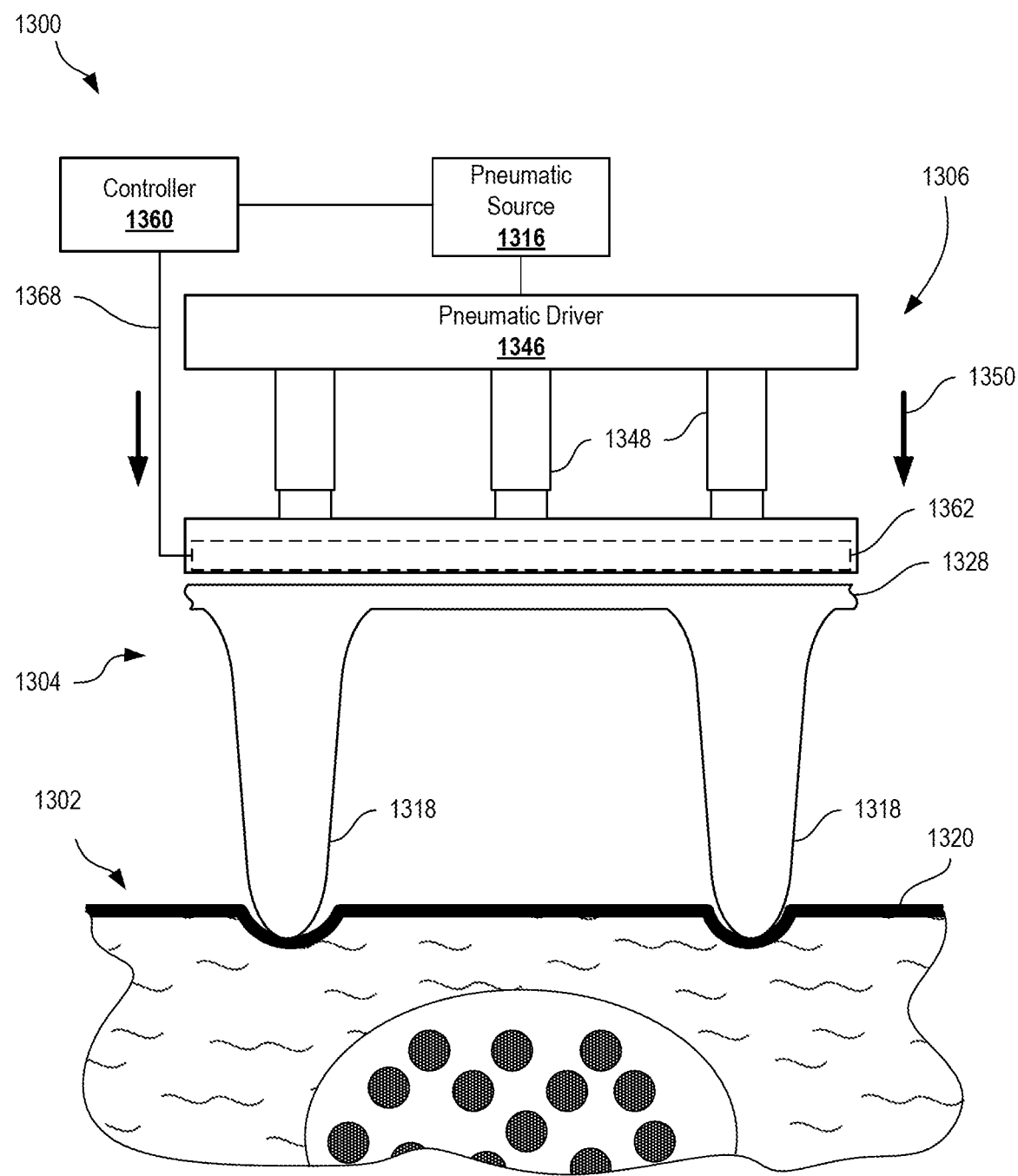
FIG. 13 is a schematic diagram depicting initial insertion of a pneumatic-driven electrode cuff into a nerve according to certain aspects of the present disclosure.
Figure 14:
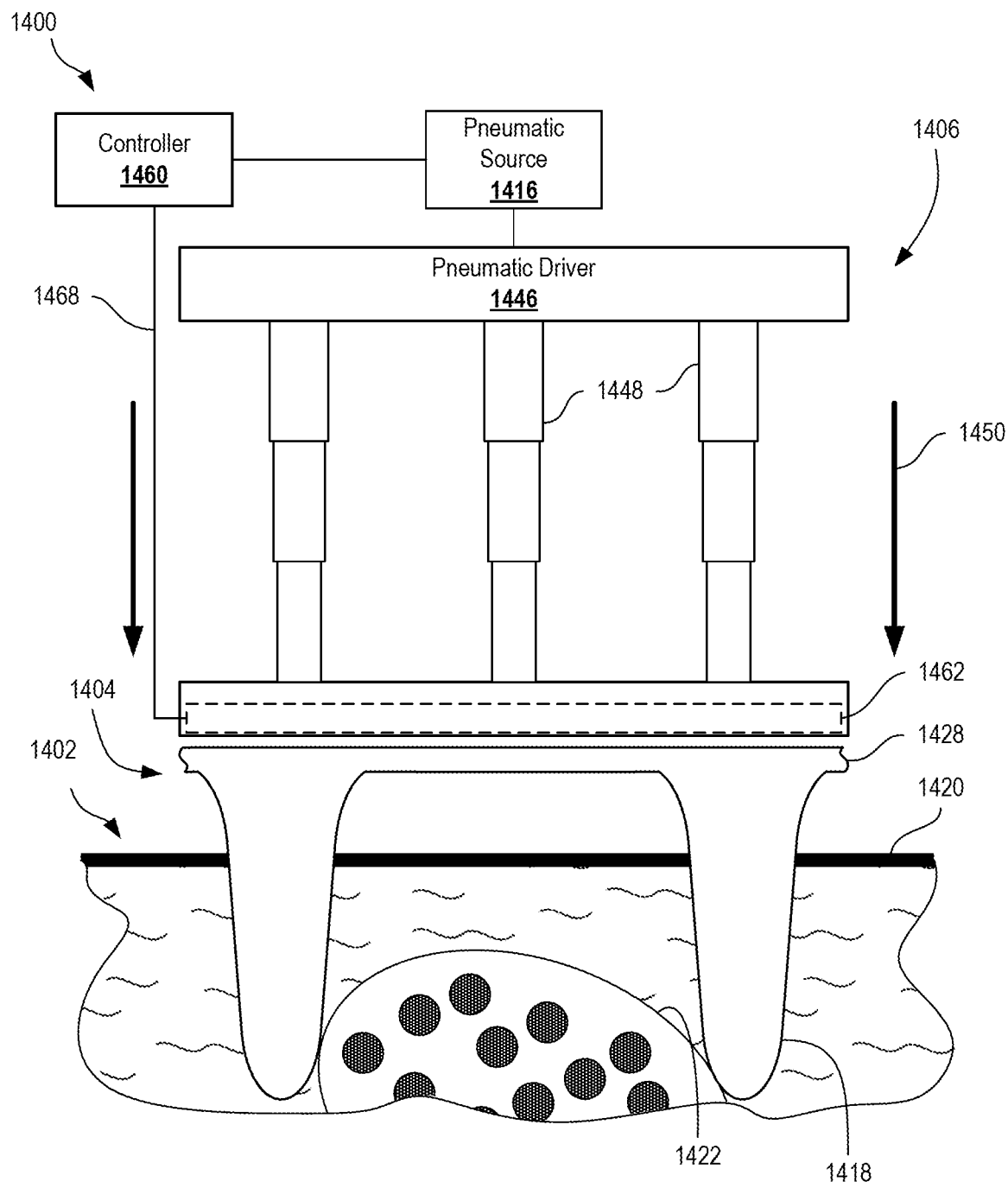
FIG. 14 is a schematic diagram depicting insertion of a pneumatic-driven electrode cuff into a nerve according to certain aspects of the present disclosure.

FIG. 13 is a schematic diagram depicting initial insertion of a pneumatic-driven electrode cuff 1304 into a nerve 1302 according to certain aspects of the present disclosure. An electrode placement system 1300 can be similar to electrode placement system 1200 of FIG. 12 when the insertion portion of implantation is underway.

During an insertion portion of implantation, compressed fluid (e.g., compressed air) from the pneumatic source 1316 can be fed into the pneumatic driver 1346. The compressed fluid can cause pistons 1348 of the pneumatic driver 1346 to extend, thus applying swift mechanical force 1350 against the substrate 1328 of the electrode cuff 1304 to urge the electrode protrusions 1318 into the epineurium 1320 of the nerve 1302. When other types of pneumatic actuators are used, the driving tool 1306 can use the compressed fluid to otherwise apply the swift mechanical force 1350, such as through the rapid expansion of bellows or an expansion chamber. The swift mechanical force 1350 can pierce the epineurium 1320 by the blunt ends of the electrode protrusions 1318.

A controller 1360 may be coupled to a pressure sensor 1362 positioned to measure force between the pneumatic driver 1346 and the electrode protrusions 1318. During the initial insertion stage, the pneumatic driver 1346 can be forcing the electrode protrusions 1318 into the epineurium 1320, thus displacing the epineurium 1320. During this stage, applied force can build up between the pneumatic driver 1346 and the epineurium 1320 until the epineurium 1320 is pierced. The pressure sensor 1362 can measure this applied force as a pressure signal. The controller 1360 can receive this signal through the sensor link 1368 and can then use that signal to control the pneumatic source 1316, thus further controlling insertion. For example, the controller 1360 can control the pneumatic source 1316 to increase applied force until it senses the epineurium 1320 has been pierced or is about to be pierced, then take necessary action to facilitate piercing the epineurium 1320 without damaging the fascicle. For example, upon sensing the epineurium 1320 has been pierced (e.g., the sensed pressure suddenly decreases after a large buildup), the controller 1360 can immediately slow, halt, or even reverse the driving force applied by the pneumatic driver 1346.

FIG. 14 is a schematic diagram depicting insertion of a pneumatic-driven electrode cuff 1404 into a nerve 1402 according to certain aspects of the present disclosure. An electrode placement system 1400 can be similar to electrode placement system 1300 of FIG. 13 after continued insertion of the electrode protrusions 1418 into the nerve 1402. The time elapsed between the electrode placement system 1300 of FIG. 13 and the electrode placement system 1400 of FIG. 14 can be very short.

As more compressed fluid is applied from the pneumatic source 1416 into the pneumatic driver 1446, the pistons 1448 can continue to rapidly extend, thus generating the swift mechanical force 1450 on the substrate of the electrode cuff to drive the electrode protrusions 1418 through the epineurium 1420 and into the nerve 1402. Despite the swift mechanical force 1450, the blunt ends of the electrode protrusions 1418 may not pierce or damage fascicles 1422 within the nerve 1402. As described above, in some cases, the electrode protrusions 1418 can have a length that is shorter than the depth of a fascicle 1422, allowing the electrodes of the electrode protrusions 1418 to be placed within the nerve 1418 and adjacent fascicles 1422 while minimizing risk of damage to fascicles 1422 during implantation of the electrode cuff 1402.

The power source 1416 can power the transducer 1442 to induce oscillations 1444 in the electrode cuff 1404. Pressure can be applied (e.g., through the driving tool 1406 and the substrate 1428) to urge the electrode protrusions 1418 into the nerve 1402. The oscillations 1444 insert the electrode protrusions 1418 through the epineurium 1420 and into the nerve 1402. Additionally, the oscillations 1444 can reduce the likelihood that an electrode protrusions 1418 would damage a fascicle 1422. For example, oscillations 1444 may move the fascicle 1422 rather than puncturing of its perineurium.

A controller 1460 may be coupled to a pressure sensor 1462 positioned to measure force between the pneumatic driver 1446 and the electrode protrusions 1418. After determining that the epineurium 1420 has been pierced, the controller 1460 can slow, halt, or reverse the driving force from the pneumatic driver 1446. The controller 1460 can then control continued driving of the electrode protrusions 1418 into the nerve 1402 until the pressure sensor 1462 senses a pressure characteristic of or associated with the electrode protrusions 1418 contacting a fascicle 1422. The controller 1460, upon determining that an electrode protrusion 1418 is contacting a fascicle 1422, can slow, halt, or reverse the driving force from the pneumatic driver 1446 to avoid damaging the fascicle 1422. In some cases, the controller 1460 can perform other actions to facilitate further insertion of the electrode protrusions 1418 without damaging the fascicle 1422, such as implementing mechanical oscillations, gentle applied force, or other actions.

Figure 15:
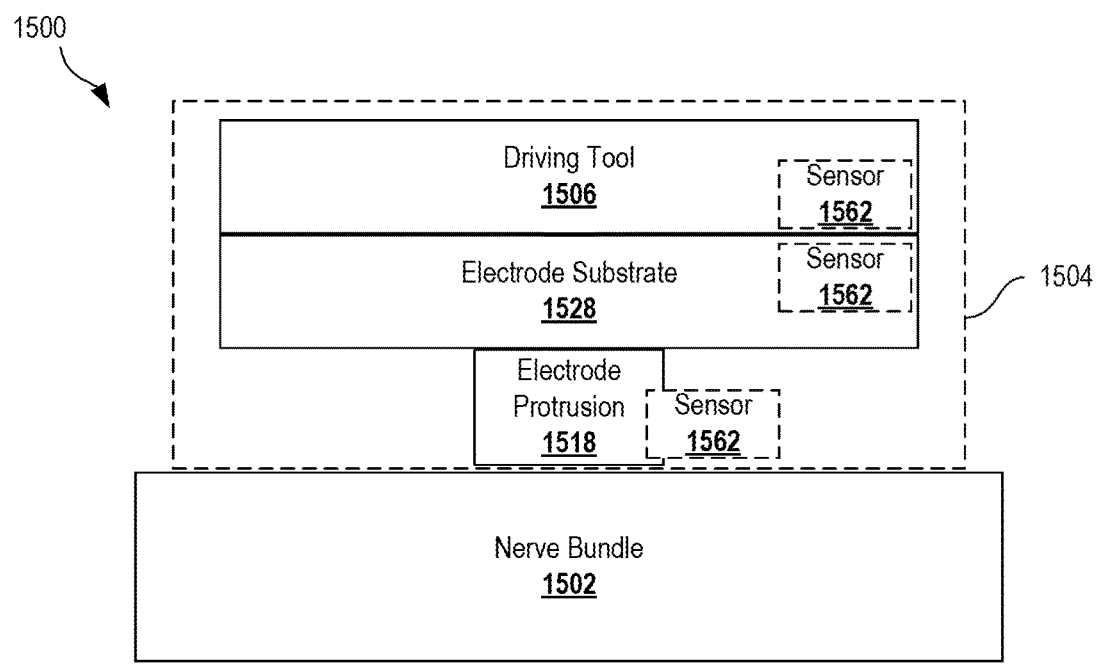
FIG. 15 is a schematic diagram depicting an electrode cuff having an integrated driving tool according to certain aspects of the present disclosure.

FIG. 15 is a schematic diagram depicting an electrode cuff 1504 having an integrated driving tool 1506 according to certain aspects of the present disclosure. The electrode placement system 1500 can include an electrode cuff 1504 having an integrated driving tool 1506. The driving tool 1506 can act on the electrode substrate 1528 to drive the electrode protrusion 1518 into the nerve 1502.

In some cases, a driving tool 1506 that is integrated into an electrode cuff 1504 can be optionally removable from the electrode cuff 1504, such as after implantation of the electrode cuff 1504.

A sensor 1562, such as sensor 862 of FIG. 8, can be coupled to, associated with, and/or integrated into the driving tool 1506 (e.g., as a pressure sensor), the electrical substrate 1528 (e.g., as a pressure sensor or electrical sensor), and/or the electrode protrusion 1518 (e.g., as an electrical sensor).

Figure 16:
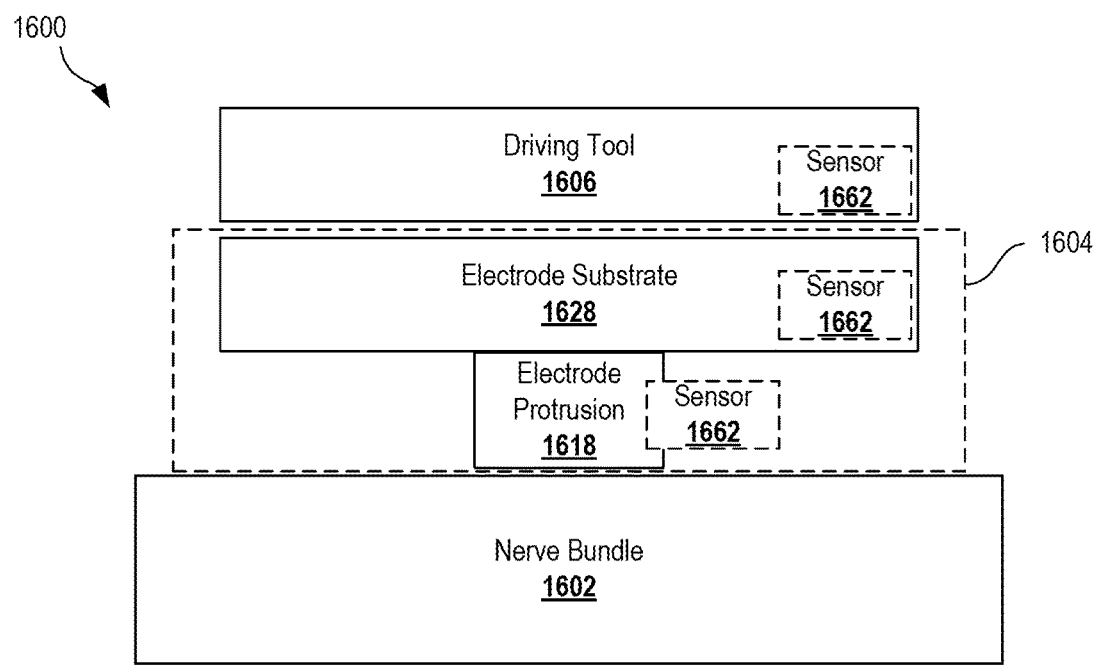
FIG. 16 is a schematic diagram depicting an electrode placement system including an electrode cuff and a separable driving tool according to certain aspects of the present disclosure.

FIG. 16 is a schematic diagram depicting an electrode placement system 1600 including an electrode cuff 1604 and a separable driving tool 1606 according to certain aspects of the present disclosure. The electrode placement system 1600 can include an electrode cuff 1604 and a separate driving tool 1606. The driving tool 1606 can act on the electrode substrate 1628 to drive the electrode protrusion 1618 into the nerve 1602.

In some cases, a driving tool 1606 that is separate from an electrode cuff 1604 can be removable couplable to the electrode cuff 1604. In some cases, a removably couplable driving tool 1606 can optionally be provided pre-coupled to the electrode cuff 1604 and can be decoupled from the electrode cuff 1604 after implantation of the electrode cuff 1604.

A sensor 1662, such as sensor 862 of FIG. 8, can be coupled to, associated with, and/or integrated into the driving tool 1606 (e.g., as a pressure sensor), the electrical substrate 1628 (e.g., as a pressure sensor or electrical sensor), and/or the electrode protrusion 1618 (e.g., as an electrical sensor).

Figure 17:
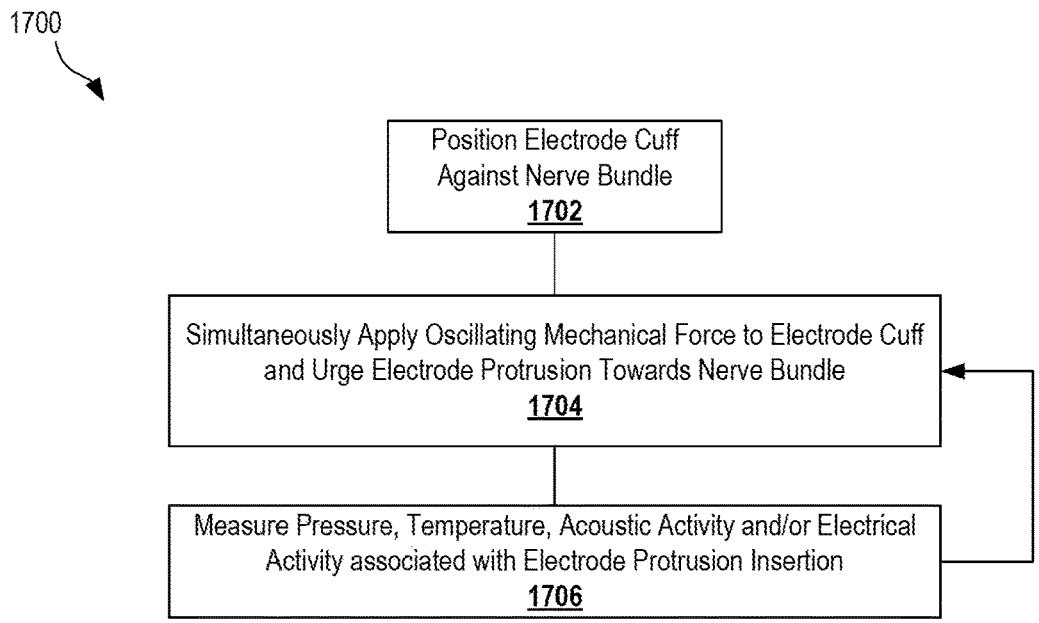
FIG. 17 is a process for implanting an electrode cuff about a nerve using an oscillating driver according to certain aspects of the present disclosure.

FIG. 17 is a process 1700 for implanting an electrode cuff about a nerve using an oscillating driver according to certain aspects of the present disclosure. At block 1702, the electrode cuff is positioned against a nerve, such as around a nerve. At block 1704, oscillating mechanical force can be applied to the electrode cuff at the same time as the electrode protrusion is urged towards the nerve. Oscillating mechanical force can include oscillations generated by a transducer, such as an ultrasonic transducer. The oscillating mechanical force can be in the ultrasonic range, such as at or greater than approximately 20 kHz. Urging the electrode protrusion towards the nerve can occur automatically due to a natural bias of the substrate of the electrode cuff to take on a particular shape, or can include application of additional force, such as using manual force or a tool (e.g., a clamp). In some cases, a pneumatic driver can apply the force urging the electrode protrusions towards the nerve.

At block 1706, pressure, temperature, acoustic activity, and/or electrical activity can be measured by a sensor, such as sensor 862 of FIG. 8. The measured pressure, temperature, acoustic activity, and/or electrical activity can be used to further control the application of oscillating mechanical force and/or the urging at block 1704.

Figure 18:
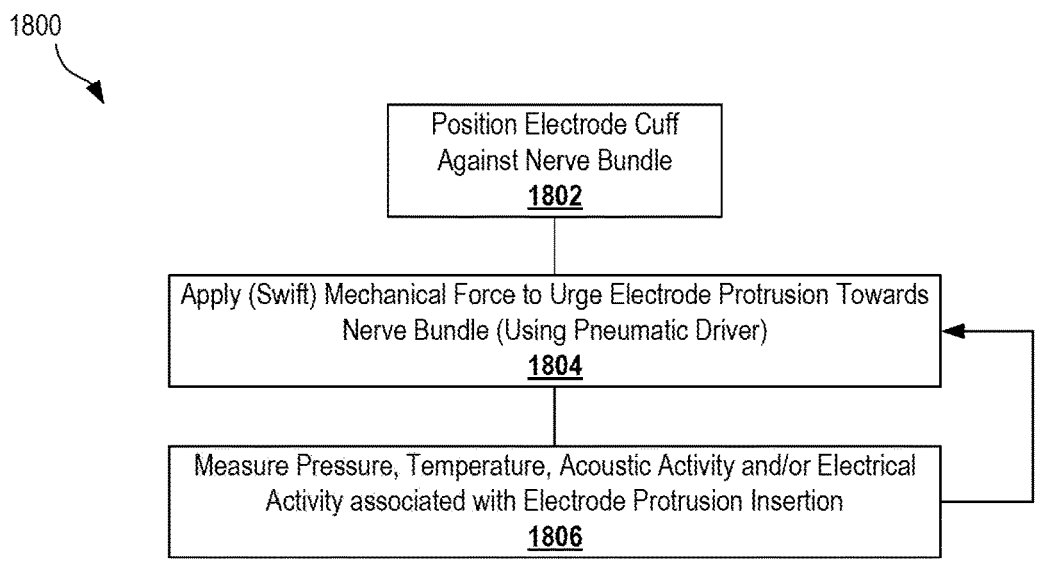
FIG. 18 is a process for implanting an electrode cuff about a nerve using a pneumatic driver according to certain aspects of the present disclosure.

FIG. 18 is a process 1800 for implanting an electrode cuff about a nerve using a mechanical driver according to certain aspects of the present disclosure. At block 1802, the electrode cuff is positioned against a nerve, such as around a nerve. At block 1804, mechanical force, such as swift mechanical force, is applied to the electrode cuff (e.g., the substrate) to urge the electrode protrusion towards the nerve. The swift mechanical force can be applied using a pneumatic driver or any other suitable driver. The pneumatic driver can be powered by a compressed fluid, such as compressed air. In some cases, mechanical oscillations can be applied to the electrode cuff at the same time as the swift mechanical force.

At block 1806, pressure, temperature, acoustic activity, and/or electrical activity can be measured by a sensor, such as sensor 862 of FIG. 8. The measured pressure, temperature, acoustic activity, and/or electrical activity can be used to further control the application of mechanical force at block 1804. In some cases, other measurements can be made at block 1806, in addition to or instead of pressure and/or electrical activity, such as temperature and/or acoustic activity.

Figure 19:
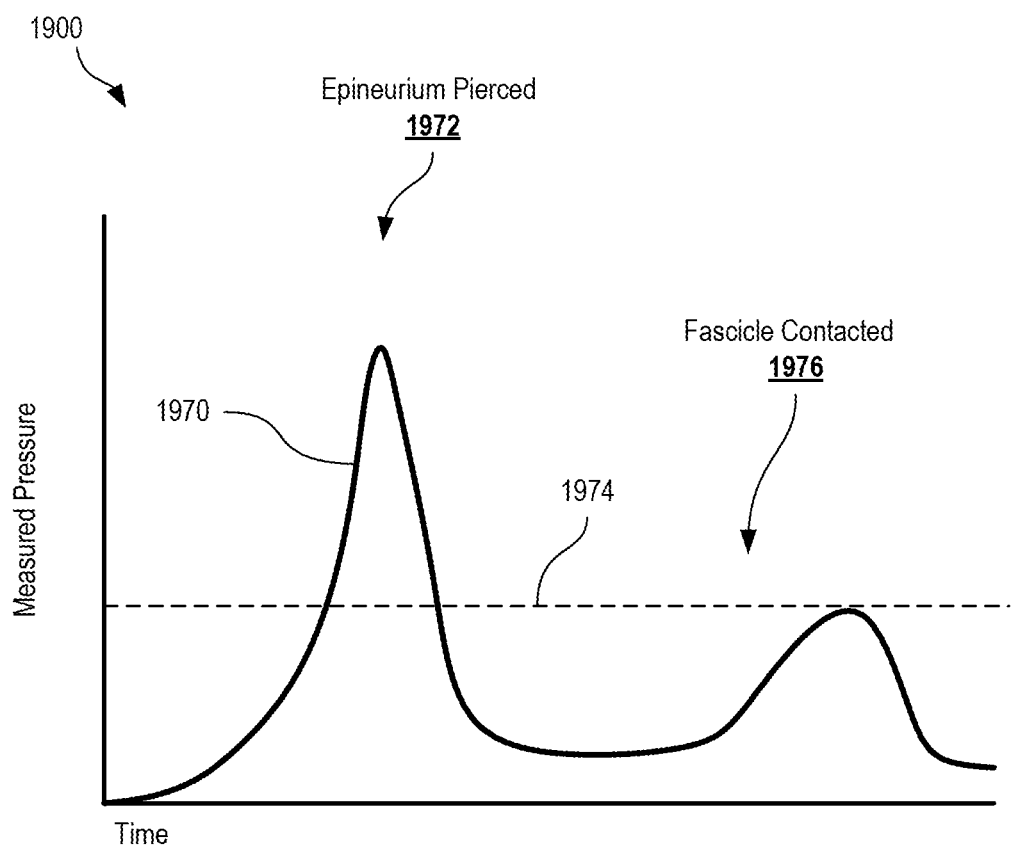
FIG. 19 is a chart depicting measured pressure with respect to time during an electrode cuff installation procedure according to certain aspects of the present disclosure.

FIG. 19 is a chart 1900 depicting measured pressure with respect to time during an electrode cuff installation procedure according to certain aspects of the present disclosure. The chart 1900 can depict installation of an electrode cuff, such as electrode cuff 804 of FIG. 8. Line 1970 indicates pressure measured by a pressure sensor, such as sensor 862 of FIG. 8. Chart 1900 is not drawn to scale and is drawn without units to provide an illustrative view of electrode cuff installation.

Initially, the measured pressure can be at or near zero or another baseline (e.g., nominal pressure to keep the electrode cuff in place around the nerve). During installation, measured pressure can build up as the electrode protrusions are pressed into the epineurium. At point 1972, the epineurium is pierced, and the measured pressure can quickly drop as the electrode protrusion enters the nerve. At this point, the controller can control the driving tool to reduce, halt, or reverse any applied force. As depicted in FIG. 19, the applied force is reduced. The measured pressure can remain relatively low while the electrode protrusion enters the nerve. At point 1976, the electrode protrusion may contact a fascicle. The resistance encountered by contacting the fascicle can cause the measured pressure to increase. The controller can allow the measured pressure to increase up to a threshold 1974. Upon reaching the threshold 1974, the controller can cause the driving tool to reduce, halt, or reverse any applied force to avoid damaging the fascicle. The threshold 1974 can be determined or pre-set to optimize insertion of electrode protrusions without damaging the fascicle. In some cases, the controller can further control the driving tool to attempt further insertion one or more additional times.

While measured pressure is depicted in FIG. 19, similar charts and procedures can be appropriately made for other measured variables, such as electrical activity (e.g., resistance), temperature, and acoustic activity. In some cases, other variables may decrease or increase or undergo other characteristic behavior whenever the epineurium is contacted and/or pierced, as well as whenever a fascicle is contacted and/or nearing damage. For example, instead of using a rapid decline in measured pressure as indication of epineurium piercing, a feedback system based on electrical resistance may detect a rapid decrease in measured resistance as the electrode protrusions enter the nerve.

Figure 20:
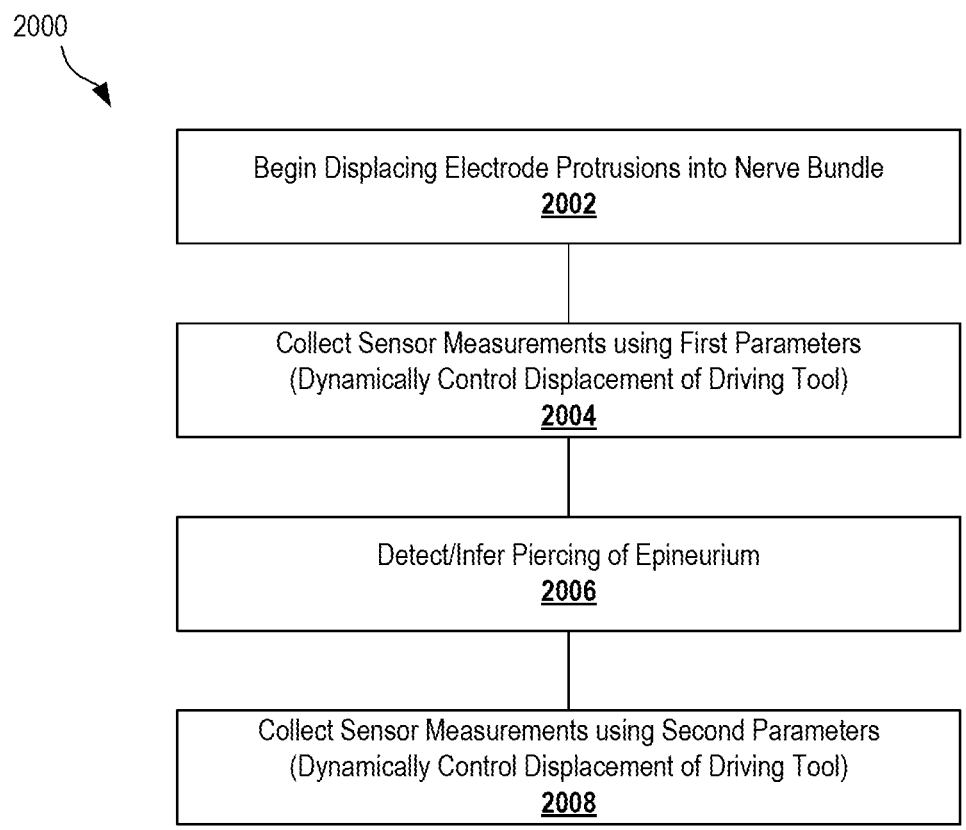
FIG. 20 is a flowchart depicting a process for controlling insertion of electrode protrusions into a nerve bundle using multiple sensor parameters according to certain aspects of the present disclosure.

FIG. 20 is a flowchart depicting a process 2000 for controlling insertion of electrode protrusions into a nerve bundle using multiple sensor parameters according to certain aspects of the present disclosure. At block 2002, electrode protrusion(s) can begin to be displaced towards and/or into a nerve bundle using a driving tool. At block 2004, sensor measurements can be collected using a first set of parameters. The first set of parameters can define how the measurements are collected and/or what measurements are collected. In some cases, a first set of parameters can include a selection of one or more sensors to use to collect data. In some cases, a first set of parameters can include a selection of one or more variables associated with one or more sensors, such as gain or sensitivity profile. In some cases, a first set of parameters can include a selection of one or more types of data to measure from one or more sensors capable of detecting different types of data, such as intensity or frequency. The sensor measurements can be used to dynamically control displacement of the driving tool to cause the electrode protrusion(s) to pierce the epineurium of the nerve bundle.

At block 2006, piercing of the epineurium can be detected and/or inferred. The detection or inference at block 2006 can be made based on measurements from the first sensor array or other sensor(s). In some cases, a user can manually provide feedback confirming and/or indicating piercing of the epineurium has occurred.

At block 2008, sensor measurements can be collected using a second set of parameters. The second set of parameters can be different from the first set of parameters. In some cases, the second set of parameters can include a different sensor or set of sensors from the first set of parameters. In some cases, the second set of parameters can include a selection of one or more variables, different from the first set of parameters, that are associated with one or more sensors, such as gain or sensitivity profile. In some cases, the second set of parameters can include a selection of one or more types of data, different from the first set of parameters, to measure from one or more sensors capable of detecting different types of data, such as intensity or frequency. The sensor measurements can be used to dynamically control displacement of the driving tool to cause the electrode protrusion(s) to become inserted deeper into the nerve bundle, such as without damaging fascicles. The second set of parameters can be automatically used upon detecting or inferring piercing of the epineurium at block 2006.

The foregoing description of the embodiments, including illustrated embodiments, has been presented only for the purpose of illustration and description and is not intended to be exhaustive or limiting to the precise forms disclosed. Numerous modifications, adaptations, and uses thereof will be apparent to those skilled in the art.

What is claimed is:

1. An electrode placement system, comprising:
   an electrode cuff comprising:
   a substrate having a tissue-facing surface curved in a concave shape;
   at least one electrode protrusion extending from the tissue-facing surface and including one or more individual electrodes thereon, each of the at least one electrode protrusion including a blunt distal end, wherein at least part of each of the one or more individual electrodes are exposed on the blunt distal end; and a driving tool positioned and configured to apply mechanical force to the substrate, the driving tool comprising an oscillating driver, a pneumatic driver, or both, wherein the driving tool is integrated into the electrode cuff.

2. The electrode placement system of claim 1, wherein the driving tool includes the oscillating driver for delivering oscillating mechanical force to the substrate of the electrode cuff.

3. The electrode placement system of claim 2, wherein the oscillating driver includes an ultrasonic transducer.

4. The electrode placement system of claim 1, wherein the driving tool includes the pneumatic driver configured to apply a swift mechanical force to the substrate of the electrode cuff.

5. The electrode placement system of claim 4, wherein the swift mechanical force is a force greater than 0.5 N.

6. The electrode placement system of claim 4, wherein the swift mechanical force is applied for less than 1 s.

7. The electrode placement system of claim 4, wherein the swift mechanical force exerts a force on the substrate of the electrode cuff that drives the electrode protrusions to penetrate a depth ranging from 2 µm to 20 µm of the nerve.

8. The electrode placement system of claim 4, wherein the swift mechanical force is a force greater than 0.5 N that is applied for less than 1 s.

9. The electrode placement system of claim 1, wherein the pneumatic driver is configured to receive a source of compressed air to provide the mechanical force.

10. The electrode placement system of claim 1, further comprising:
   a sensor coupled to the at least one electrode protrusion to measure an insertion-indicative value, the insertion-indicative value being indicative of whether the at least one electrode protrusion has penetrated at least part of the nerve; and
   a controller coupled to the sensor and the driving tool to control the driving tool in response to the measured value.

11. The electrode placement system of claim 10, wherein the sensor comprises an electrical sensor, a mechanical sensor, a temperature sensor, or an acoustic sensor.

12. The electrode placement system of claim 10, wherein the driving tool includes at least one pneumatic actuator, and wherein the sensor is a pressure sensor for detecting pneumatic pressure applied to the at least one pneumatic actuator.

13. A method of applying an electrode cuff to target nerve, comprising:
   providing an electrode cuff comprising:
      a substrate having a tissue-facing surface curved in a concave shape; and
      at least one electrode protrusion extending from the tissue-facing surface and including one or more individual electrodes thereon, the at least one electrode protrusion includes a blunt distal end, wherein at least part of the one or more individual electrodes are exposed on the blunt distal end; and
   positioning the tissue-facing surface of the substrate against a nerve; and
   actuating a driving tool to apply a mechanical force to the electrode cuff to pierce the at least one protrusion into a nerve, wherein the driving tool is an oscillating driver, a pneumatic driver, or both, wherein the driving tool is integrated into the electrode cuff.

14. The method of claim 13, further comprising:
   measuring an insertion-indicative value, the insertion-indicative value being indicative of whether the at least one electrode protrusion has penetrated at least part of the nerve;
   wherein actuating the driving tool further comprises dynamically controlling the mechanical force applied to the substrate in response to the measured insertion-indicative value.

15. The method of claim 13, wherein the driving tool includes the oscillating driver, wherein actuating the oscillating driver comprises applying oscillating mechanical force to the electrode cuff to pierce the at least one protrusion into the nerve.

16. The method of claim 13, wherein the driving tool includes the pneumatic driver, wherein actuating the pneumatic driver comprises applying swift mechanical force to the electrode cuff to pierce the at least one protrusion into the nerve.

17. The method of claim 16, wherein the swift mechanical force is a force greater than 0.5 N that is applied for less than 1 s.

* * * * *